United States Patent
Fujinuma et al.

(10) Patent No.: US 8,388,696 B2
(45) Date of Patent: Mar. 5, 2013

(54) TWO-PART HAIR DYE OR BLEACH COMPOSITION

(75) Inventors: Hiroyuki Fujinuma, Sumida-ku (JP);
Shuhei Matsumoto, Sumida-ku (JP);
Tetsuya Chiba, Sumida-ku (JP);
Yoshinori Inagawa, Sumida-ku (JP);
Daisuke Kodama, Sumida-ku (JP)

(73) Assignee: Kao Corporation, Tokyo (JP)

( * ) Notice: Subject to any disclaimer, the term of this patent is extended or adjusted under 35 U.S.C. 154(b) by 9 days.

(21) Appl. No.: 12/529,553

(22) PCT Filed: Apr. 25, 2008

(86) PCT No.: PCT/JP2008/058137
§ 371 (c)(1),
(2), (4) Date: Sep. 2, 2009

(87) PCT Pub. No.: WO2008/136441
PCT Pub. Date: Nov. 13, 2008

(65) Prior Publication Data
US 2010/0126523 A1      May 27, 2010

(30) Foreign Application Priority Data
Apr. 27, 2007  (JP) ................................. 2007-120360

(51) Int. Cl.
*A61Q 5/10*         (2006.01)
(52) U.S. Cl. .............. 8/405; 8/431; 8/457; 8/477; 8/526
(58) Field of Classification Search .............. 8/405, 431, 8/457, 526, 477
See application file for complete search history.

(56) References Cited

U.S. PATENT DOCUMENTS

| | | |
|---|---|---|
| 3,341,418 A | 9/1967 | Moses, et al. |
| 3,709,437 A | 1/1973 | Wright |
| 4,509,661 A | 4/1985 | Sugizaki et al. |
| 4,823,985 A | 4/1989 | Grollier et al. |
| 4,961,925 A | 10/1990 | Tsujino et al. |
| 5,064,103 A | 11/1991 | Bennett |
| 5,143,518 A | 9/1992 | Madrange et al. |
| 5,848,730 A | 12/1998 | Kawase et al. |
| 5,968,486 A | 10/1999 | Newell et al. |

(Continued)

FOREIGN PATENT DOCUMENTS

| | | |
|---|---|---|
| DE | 1801518 | 1/1971 |
| EP | 0 113 418 | 7/1984 |

(Continued)

OTHER PUBLICATIONS

U.S. Appl. No. 12/739,835, filed Apr. 26, 2010, Fujinuma, et al.

(Continued)

*Primary Examiner* — Eisa Elhilo
(74) *Attorney, Agent, or Firm* — Foley & Lardenr LLP

(57) ABSTRACT

The invention is directed to a two-part hair cosmetic for hair dyeing or bleaching which includes a first agent containing an alkaline agent and a second agent containing hydrogen peroxide and a squeeze container for discharging a mixed solution of the first agent and the second agent. The first agent or second agent contains a foaming agent. The mixed solution thereof has a viscosity (25° C.) of from 1 mPa·s to 100 mPa·s. The ratio between the total volume of the first and second agents and the inner volume of the container body is in the range of from 0.30 to 0.60.

28 Claims, 8 Drawing Sheets

U.S. PATENT DOCUMENTS

| | | |
|---|---|---|
| 7,938,864 B2 | 5/2011 | Miyabe et al. |
| 7,955,400 B2 | 6/2011 | Fujinuma et al. |
| 8,002,848 B2 | 8/2011 | Miyabe |
| 8,025,702 B2 | 9/2011 | Fujinuma et al. |
| 8,025,703 B2 | 9/2011 | Ogawa et al. |
| 2004/0213752 A1 | 10/2004 | Fujinuma et al. |
| 2010/0126522 A1 | 5/2010 | Fujinuma et al. |
| 2010/0126523 A1 | 5/2010 | Fujinuma et al. |
| 2010/0251488 A1 | 10/2010 | Fujinuma et al. |
| 2010/0316583 A1 | 12/2010 | Fujinuma et al. |
| 2011/0073128 A1 | 3/2011 | Ogawa et al. |
| 2011/0214682 A1 | 9/2011 | Fujinuma et al. |
| 2011/0277782 A1 | 11/2011 | Iijima et al. |

FOREIGN PATENT DOCUMENTS

| | | |
|---|---|---|
| EP | 0 503 507 | 9/1992 |
| EP | 1 055 425 | 11/2000 |
| EP | 0 877 653 | 10/2002 |
| EP | 1 291 006 | 12/2003 |
| EP | 1470 812 A1 * | 4/2004 |
| EP | 1 470 812 A1 | 10/2004 |
| GB | 1125528 | 8/1968 |
| GB | 2 254 341 | 10/1992 |
| GB | 2 293 157 | 3/1996 |
| JP | 48-068750 | 9/1973 |
| JP | 49-050144 | 5/1974 |
| JP | 55-49308 | 4/1980 |
| JP | 58-030282 | 6/1983 |
| JP | 59-108710 | 6/1984 |
| JP | 60-020262 B2 | 5/1985 |
| JP | 61-143412 | 7/1986 |
| JP | 62-242609 | 10/1987 |
| JP | 63-246313 | 10/1988 |
| JP | 04-99711 | 3/1992 |
| JP | 04-282307 | 10/1992 |
| JP | 04-282308 | 10/1992 |
| JP | 04-293568 | 10/1992 |
| JP | 05-051755 | 7/1993 |
| JP | 06-107530 | 4/1994 |
| JP | 06-271435 | 9/1994 |
| JP | 07-23293 | 3/1995 |
| JP | 7 215352 | 8/1995 |
| JP | 7 215353 | 8/1995 |
| JP | 2001-267834 | 10/1995 |
| JP | 07-330559 | 12/1995 |
| JP | 07-330560 | 12/1995 |
| JP | 08-040837 | 2/1996 |
| JP | 08-119838 | 5/1996 |
| JP | 08-119839 | 5/1996 |
| JP | 08-165235 | 6/1996 |
| JP | 08-199188 | 8/1996 |
| JP | 08-230959 | 9/1996 |
| JP | 08-231345 | 9/1996 |
| JP | 08-231346 | 9/1996 |
| JP | 08-259426 | 10/1996 |
| JP | 08-268848 | 10/1996 |
| JP | 08-283695 | 10/1996 |
| JP | 09-002923 | 1/1997 |
| JP | 09-002925 | 1/1997 |
| JP | 09-025223 | 1/1997 |
| JP | 09-040534 | 2/1997 |
| JP | 2579516 | 2/1997 |
| JP | 09-136818 | 5/1997 |
| JP | 09-143040 | 6/1997 |
| JP | 09-506130 | 6/1997 |
| JP | 9 227347 | 9/1997 |
| JP | 09-234112 | 9/1997 |
| JP | 09-255541 | 9/1997 |
| JP | 09-301835 | 11/1997 |
| JP | 10-000397 | 1/1998 |
| JP | 10-025230 | 1/1998 |
| JP | 10 167938 | 6/1998 |
| JP | 10-287534 | 10/1998 |
| JP | 10-324357 | 12/1998 |
| JP | 11-018836 | 1/1999 |
| JP | 11-018837 | 1/1999 |
| JP | 11-50089 | 2/1999 |
| JP | 11-124321 | 5/1999 |
| JP | 11-139945 | 5/1999 |
| JP | 11-199454 | 7/1999 |
| JP | 11-206454 | 8/1999 |
| JP | 11-246369 | 9/1999 |
| JP | 11-286421 | 10/1999 |
| JP | 11-349453 | 12/1999 |
| JP | 2000-191471 | 7/2000 |
| JP | 2000-128215 | 9/2000 |
| JP | 2000-297018 | 10/2000 |
| JP | 2000-297019 | 10/2000 |
| JP | 2001-010930 | 1/2001 |
| JP | 2001-039460 | 2/2001 |
| JP | 2001-097834 | 4/2001 |
| JP | 2001-172166 | 6/2001 |
| JP | 2001-278742 | 10/2001 |
| JP | 2001-288054 | 10/2001 |
| JP | 2001-327321 | 11/2001 |
| JP | 2002-020247 | 1/2002 |
| JP | 2002-97121 | 4/2002 |
| JP | 2002-154938 | 5/2002 |
| JP | 2002-193771 | 7/2002 |
| JP | 2002-220329 | 8/2002 |
| JP | 2002-226340 | 8/2002 |
| JP | 2002-226344 A | 8/2002 |
| JP | 2002-284655 | 10/2002 |
| JP | 03-012479 | 1/2003 |
| JP | 2003-26554 | 1/2003 |
| JP | 2003-040747 | 2/2003 |
| JP | 2003-063936 | 3/2003 |
| JP | 2003-073240 | 3/2003 |
| JP | 2003-073241 | 3/2003 |
| JP | 2003-081791 A | 3/2003 |
| JP | 2003-095900 | 4/2003 |
| JP | 2004 339216 | 12/2004 |
| JP | 2004-339216 | 12/2004 |
| JP | 2006-124279 | 5/2006 |
| JP | 2006 124279 | 5/2006 |
| JP | 2007-291015 A1 | 11/2007 |
| JP | 2007-314523 A1 | 12/2007 |
| JP | 2010-6803 | 1/2010 |
| JP | 2010-006805 | 1/2010 |
| JP | 2001-019626 | 1/2011 |
| WO | WO-91/14759 | 10/1991 |
| WO | WO-95/16023 | 6/1995 |
| WO | WO-01/85105 | 11/2001 |
| WO | WO-01/85113 | 11/2001 |
| WO | WO2009/054027 A1 | 4/2009 |
| WO | WO2009/054028 A1 | 4/2009 |
| WO | WO2009/054029 A1 | 4/2009 |
| WO | WO2009/054147 A1 | 4/2009 |
| WO | WO2009/054148 A1 | 4/2009 |

OTHER PUBLICATIONS

U.S. Appl. No. 12/739,091, filed Apr. 21, 2010, Fujinuma, et al.
U.S. Appl. No. 12/739,610, filed Apr. 23, 2010, Fujinuma, et al.
U.S. Appl. No. 12/739,471, filed Apr. 23, 2010, Miyabe, et al.
U.S. Appl. No. 12/739,631, filed Apr. 23, 2010, Miyabe.
Saito, H., "Foamer Yoki No Tokucho To Saikin No Gijutsu Doko", Fragrance Journal, vol. 34, No. 7, pp. 54-59 and 123 (Jul. 15, 2006).
Food & Packaging, vol. 35, No. 10, pp. 588-593 (1994) (with English translation).
Food & Packaging, vol. 34, No. 9, pp. 531-535 (1993) (with English translation).
U.S. Appl. No. 12/532,934, filed Sep. 24, 2009, Fujinuma, et al.
U.S. Appl. No. 12/995,378, filed Nov. 30, 2010, Ogawa, et al.
U.S. Appl. No. 12/769,182, filed Apr. 28, 2010, Fujinuma, et al.
U.S. Appl. No. 13/107,183, filed May 13, 2011, Fujinuma, et al.
U.S. Appl. No. 13/146,157, filed Jul. 25, 2011, Iijima, et al.
Taya-A.T. HM Education Mook., Series 3. "Knowing Mechanisms of Hair Coloring Agents." Apr. 10, 1998. pp. 8-9. (with English translation).
Nakanishi, Fumio. Fragrance Journal. "Future View of Hair Care Products." Jan. 15, 1997. pp. 49-56. (with English translation).
Sato, Takatoshi, et al. Fragrance and Cosmetics Science. "Permanent Hair Colorant." Sep. 20, 2001. pp. 138-140. (with English translation).

Watanabe, Yasushi, et al. Hair Science. "Hair Colorant." Feb. 1, 1986. pp. 144-150. (with English translation).
Miyagi, Takashi. Foods and Containers, vol. 42, No. 10. "Growing Pump Foamer Spreading into Western Markets, Part One: Mini-Foamer." Oct. 1, 2001. pp. 609-613. (with English translation).
Kishi, Haruo. Modern Fragrance and Cosmetics Science, $1^{st}$ Edition. Mar. 20, 1979. pp. 42-47. (with English translation).
Cosmetics Handbook. Nov. 1, 1996. pp. 220-221, 441-444. (with English translation).
Handbook—Raw Materials of Cosmetics and Drugs—revised edition. Feb. 1, 1977. pp. 358-361. (with English translation).
Yasuda, Kosaku, et al. Knowledge of Fat and Oil Products. Aug. 25, 1977. pp. 240-244. (with English translation).
Mitsui, Takeo. New Cosmetic Science. Jan. 12, 1993. pp. 137-142. (with English translation).
The Handbook of Oil Chemistry, $4^{th}$ ed. "Lipids and Surfactants." Nov. 20, 2001. p. 522. (with English translation).
Comprehensive Dictionary of Chemistry. Oct. 20, 1989. pp. 56, 60-61, 646-647, 1762-1763. (with English translation).
Sato, Takatoshi, et al. Fragrance and Cosmetics Science. Mar. 20, 1997. pp. 73-74. (with English translation).
Japanese Collection of General Raw Materials for Cosmetics, fourth edition. Oct. 31, 1997. p. 583. (with English translation).
Analytical Chemistry Handbook, revised second edition. Oct. 10, 1971. pp. 27-29. (with English translation).
Analysis Methods for Surfactants. Oct. 1, 1975. pages 117-118. (with English translation).
Chemical Daily. "Surfactant—Penetrated to the various fields taking advantage of unique characteristics." Jan. 21, 1999. (with English translation).
The Nikkan Kogyo Shimbun, Ltd. "Nonylphenol Identified as Endocrine Disrupting Chemical." Aug. 6, 2001. (with English translation).
Chemical Daily. "Surfactant—Started growing responding to safety requirement." Jan. 19, 2000. (with English translation).
Chemical Daily. "Surfactant—Remarkable performance of non-ionic surfactant (Market conditions in chemicals)." Jan. 25, 2002. (with English translation).
Nakanishi, Fumio, et al. Science History of Hair Dye. Jan. 8, 1991. pp. 45-47. (with English translation).
Experiment Result Report 1 (with English translation), prepared on Jul. 11, 2011, in regard to No. 22009, 2011 (yo).
Experimental Result Report 2 (with English translation), prepared on Jul. 22, 2011, in regard to No. 22009, 2011 (yo).
Declaration by Akiko Nagabuchi (with English translation), served on Sep. 21, 2011, in regard to No. 22009, 2011 (yo).
Experiment Result Report 5 (with English translation), served on Sep. 21, 2011, in regard to No. 22009, 2011 (yo).
Arai, Yasuhiro. "State-of-the-art: Hair Color Technology—Trends in development as seen in patents." Published by Fragrance Journal Ltd. Aug. 25, 2004. pp. 102-105, 212-213. (with English translation).
Experimental Result Report 6 (with English translation), served on Sep. 21, 2011, in regard to No. 22009, 2011 (yo).
Experimental Result Report 7 (with English translation), served on Sep. 21, 2011, in regard to No. 22009, 2011 (yo).
Hayakawa, Masakatsu. Fragrance Journal. "Trends in the R&D of Hair Dyes and Issues to Address." No. 38 (vol. 7, No. 5) Sep. 25, 1979. pp. 41-44. (with English translation).
Written Argument filed by the Debtor (1/2) in The Case of Request for Provisional Disposition of Patent Right: No. 22056, 2011 (yo), served on Sep. 6, 2011. pp. 1-5, 29-34. (with partial English translation).
Amendments to the Claims in Japanese Patent Application No. 2010-268209, filed on Apr. 8, 2011. (with English translation).
Publication of Unexamined Patent Application JP 2003-81369, Mar. 19, 2003.
Statements of Grounds of Appeal dated Aug. 10, 2011 in corresponding European Patent Application No. 08 752 171.2.
European Office Action dated Sep. 27, 2011 in corresponding European Patent Application No. 08 752 171.2.
Communication from Hoffman-Eitle dated Oct. 21, 2011 in corresponding European Patent Application No. 08 752 171.2.
Third Party Observations in accordance with Article 115, EPC, in corresponding European Patent Application No. 08 752 171.2.

European Office Action dated Nov. 30, 2011 in corresponding European Patent Application No. 08 752 171.2.
"Make Your Hair Beautiful by Correct Usage—Hair Coloring ABC, revised edition." Feb. 1, 2000, pp. 18-19 (with English Translation).
Amendment filed Dec. 5, 2008 in European Patent application No. 0 400 9836.0.
Amendment filed Sep. 10, 2010 in Japanese application No. 2004-130373 (w/ English Translation).
Close-up photocopy of the folding, collapsible box for "Poly Brillance Intensiv-Color-Crème" Aug. 25, 1997.
Communication Pursuant to Article 94(3) EPC issued Dec. 29, 2008 in European Patent application No. 0 400 9836.0.
Communication Pursuant to Article 94(3) EPC issued Jun. 28, 2010 in European Patent application No. 0 400 9836.0.
Communication Pursuant to Article 94(3) EPC issued Nov. 5, 2010 in European Patent application No. 0 400 9836.0.
Comprehensible Surfactant, first edition, Sep. 1, 2003 pp. 32-49, (with English translation).
Office Action in JP Application No. 2004-130373 dated Jul. 22, 2008.
Cosmetics Dictionary, first edition, Oct. 1, 1992, p. 373, (with English translation).
Decision of Refusal issued Jun. 16, 2010 in Japanese application No. 2004-130373 (w/ English Translation).
Decision to Refuse a European Patent Application issued Apr. 19, 2011, in regard to European Patent Application No 087521712, filed Apr. 25, 2008.
Declaration by Hattori, Nobuhito, in regard to No. 22056, 2011 (yo), served on Dec. 28, 2011 (with English translation).
Denavarre, Maison G, The Chemistry and Manufacture of Cosmetics, second edition, vol. 4, 1975 pp. 841-863.
Dr Matthias Schweinsberg, Test Report: Foaming Characteristics and Flow Characteristics of Cosmetic Products According to EP 1 291 006 AI, Feb. 17, 2012 with English Translation, served on Apr. 17, 2012 in regard to DE litigation No. 4a 028/11.
English translation of Amendment filed Mar. 9, 2009 in Japanese application No. 2004-130373.
English Translation of Decision to Grant a Patent issued Jan. 4, 2011, in Japanese Patent application No. 2004-130373 w/ Copy of Allowed Claims.
English Translation of Decision to Grant a Patent issued Jan. 4, 2011, in Japanese Patent application No. 2008-270377 w/ Allowed Claims.
English translation of Notification of Reasons for Refusal issued Jan. 6, 2009 in Japanese application No. 2004-130373.
English translation of Notification of Reasons for Refusal issued Jul. 22, 2008, in Japanese Application No. 2004-130373.
English translation of Remarks filed Mar. 9, 2009 in Japanese application No. 2004-130373.
English translation of Remarks filed Oct. 20, 2008 in Japanese application No. 2004-130373.
English translation of Submission of Publication and the like, dated Dec. 25, 2007, in Japanese Patent Application No. 2004-130373.
English translation of Submission of Publication and the like, dated Feb. 29, 2008, in Japanese Patent Application No. 2004-130373.
English translation of Submission of Publications and the like, filed Mar. 24, 2009, in Japanese Application No. 2004-130373.
English translation of Submission of Publications and the like, filed Nov. 10, 2008, in Japanese Application No. 2004-130373.
English translation of Submission of Publications and the like, filed Sep. 7, 2009, in Japanese Application No. 2004-130373.
Entire contents of the folding, collapsible box for "Poly Brillance Intensiv-Color-Crème" Aug. 25, 1997.
European Patent Office Communication issued Mar. 12, 2012 in European Patent Application 04 009 836 0.
European Patent Office Communication pursuant to Rule 114(2) EPC issued May 3, 2011, in European Application No. 04009836 0 filed Apr. 26, 2004.
European Search Report submitted Aug. 23, 2004, in European Patent Application No. 04009836 0.
Excerpt from the Internet Website: www bagonvalve corn in regard to Request Cancelation in Utility Model 20 2004 021 775, served on Apr. 18, 2012, (3 pp).
Experimental Report 1 (with English translation), served on May 24, 2011, in regard to Heisei 23 year (Yo) No. 22009.

Experimental Report 2 (with English translation), served on May 25, 2011, in regard to Heisei 23 year (Yo) No. 22009.
Experimental Report 3 (with English translation), served on May 25, 2011, in regard to Heisei 23 year (Yo) No. 22009.
Experimental Result Report 13 (with English translation), served on Jan. 30, 2012, in regard to No. 22009, 2011 (yo).
Experimental Result Report 8 (with English translation), served on Nov. 29, 2011, in regard to No. 22009, 2011 (yo).
Extended European Search Report issued Apr. 7, 2011, in European Application No. 10183376 2.
Extended European Search Report issued in Nov. 4, 2010 in European Patent Application No. 10172766 7.
Feminine Treatment Hair Color 84, Certification for Approval for Manufacture of Quasi-Drug (with English Translation), Jan. 30, 1997.
Food and Packaging, vol. 34, No. 8, "Can Technology Study Group" Aug. 1, 1993, 6 pages.
Fragrance Journal, vol. 19, No. 6, "Recent Progress of Hair Dyes and Problems in Research and Development ", Jun. 15, 1991, pp. 26-27 (with English translation).
Hair Mode, Aug. 1996, No. 437, p. 108 (with partial English translation).
Handbook, "Poly Haarberater Coloration," original edition, 1992, pp. 76-77.
Henkel Study Report, Study No. 1100546-1 "Open Epicutaneous Test," served on Jan. 30, 2012, in regard to No. 22009, 2011 (yo).
Henkel Study Report, Study No. 1100546-2 "Single Application Epicutaneous Patch Test (24th Patch Test)," served on Jan. 30, 2012, in regard to No. 22009, 2011 (yo).
Henkel Study Report "In Vitro Skin Irritation Test: Human Skin Model Test," served on Jan. 30, 2012, in regard to No. 22009, 2011 (yo).
Instructions for Feminine Retouch Color (with English Translation), Feminine Co, Ltd, published before Apr. 23, 2003 (served on May 25, 2011, in regard to Heisei 23 year (Yo) No. 22009).
Instructions for Feminine Treatment Hair Color (with English Translation), Feminine Co, Ltd, published before Apr. 23, 2003 (served on May 25, 2011 in regard to Heisei 23 year (Yo) No. 22009).
Instructions for use contained in the folding, collapsible box for "Poly Brillance Intensiv-Color-Crème" Aug. 25, 1997.
Ishikawa, Ryoji Experimental Report, in regard to No. 22056, 2011 (yo) Dec. 27, 2011, (with English translation).
Iwakura, Ryouhei "Present State and Problems of Hair Dyes", Fragrance Journal, Special Issue No. 11, pp. 87-93, Dec. 25,1990. (with English translation).
Japanese Patent Office Communication Apr. 21, 2009, 3 pp (includes statement submitted by third party).
Miyagi, Takashi Food and Container, vol. 35, No. 10, pp. 588-593, 1994 (with English translation).
Miyagi, Takashi Food and Container, vol. 35, No. 11, pp. 624-627, 1994 (with English translation).
Miyagi, Takashi Food and Packaging, vol. 34, No. 8, "Does Non-Gas Container Cause a Boom? (Part 2)", 1993, pp. 467-471. (with English translation).
Miyagi, Takashi Food and Packaging, Vol 34, No. 9, "Will Non-Gas Containers Create a Boom? (No. 3)" 1993 pp. 531-535. (with English translation).
Miyagi, Takashi Food and Packaging, vol. 36, No. 3, "Non-Gas Container Having Increased Level of Accomplishment (Part 3)", 1995, pp. 154-158. (with English translation).
Mottram, F. J., et al. Poucher's Perfumes, Cosmetics and Soaps, 10th ed., © 2000, "Hair Shampoos", pp. 295-301.
Murata, Seishiro, Cosmetic Dictionary, 1st edition, pp. 182-183, 666-667, Dec. 15, 2003 (with English translation).
Nakanishi, Fumio, Fragrance Journal, "Function of Recent Hair Coloring Agent and Developmental Trend Thereof ", Aug. 15, 2001, pp. 39-45. (with English translation).
Nakanishi, Fumio Fragrance Journal "Recent Progress and Prospective Problems in Hair Colorants and Hair Lighteners" vol. 25, No. 1 Jan. 15, 1997 pp. 49-56 (with English translation).
Notice of Reasons for Rejection in JP Appln No. 2008-115372 dated Sep. 4, 2012.
New Cosmetic Science, second edition, Jan. 18, 2001, pp. 152-153. (with English translation).
Notification of Reason for Refusal, dated Jul. 22, 2008, in Japanese Patent Application No. 2004-130373.
Observations under Rule 114(2) EPC filed Apr. 9, 2010, in European Patent application No. 0 400 9836 0.
Office Action issued Nov. 5, 2010, in EP Application No. 04 009 836 0.
Omura, Takayuki, et al. Fragrance Journal, "Development Trend and Problems of Recent Hair Foam", Mar. 15, 1994, pp. 29-35, (with English translation).
Pharmaceutical Additive Dictionary, 2nd edition, pp. 153-154, 203-205, Mar. 25, 2002. (with English translation).
Photocopy of a folding, collapsible box for "Poly Brillance Intensiv-Color-Creme", dated as Aug. 25, 1997.
Prettia Product Information (with English Translation), Kao Corporation, published after Apr. 23, 2003 (served on May 25, 2011 in regard to Heisei 23 year (Yo) No. 22009).
Quasi Drugs Manufacturing Material Specification 2006, first edition, pp. 527-528, Jun. 16, 2006. (with English translation).
Remarks filed Feb. 25, 2011 in European Patent application No. 08 752 171 2.
Reply to EESR in European Patent Application No. 10172766.7, Apr. 29, 2011.
Response to Communication filed Aug. 10, 2010 in European Patent application No. 0 400 9836.0.
Response to Communication filed Feb. 18, 2011 in European Patent application No. 0 400 9836.0.
Response to Communication filed Jul. 8, 2009 in European Patent application No. 0 400 9836.0.
Response to Communication Pursuant to Article 96(2) EPC filed Apr. 25, 2007 in European Patent application No. 0 400 9836.0.
Robbins, Clarence R., "Chemical and Physical Behavior of Human Hair, fourth edition " Jul. 10, 2006, pp. 221-231. (with English translation).
Rompps Chemie Lexikon, vol. 6, 8th Ed., 1998, p. 4531.
Sato, Takatoshi Science of Cosmetics, Mar. 20, 1997, pp. 138-140. (with English translation).
Shinbiyo Marcel Oct. 1996 No. 31, pp. 73 and 83 "Vivid Highlight" advertisement page (with partial English translation).
Study Report, No. 1100547-1, "Dermatological Use Test with Hair-Coloring Products in Split Design," served on Jan. 30, 2012, in regard to No. 22009, 2011 (yo).
Submission of Publication and the like, dated Sep. 7, 2009, in Japanese Patent Application No. 2004-130373.
Submission of Publication issued Oct. 18, 2010, in JP Application No. 2004-130373 (with English translation).
Submission of Publications and the like, dated Mar. 24, 2009, in Japanese Patent Application No. 2004-130373 (with English translation).
Submission of Publications and the like, dated Nov. 10, 2008, in Japanese Patent Application No. 2004-130373.
Submission of Publications and the like, filed Apr. 8, 2009 in Japanese application No. 2004-130373 (w/ English Translation).
Submission of Publications and the like, filed Oct. 18, 2010 in Japanese application No. 2004-130373 (w/ English Translation).
Submission of Publications and the like, filed Oct. 25, 2010 in Japanese application No. 2008-270377 (w/ English Translation).
Tashima, Masaru et al. Fragrance Journal "Research and Development of Mist Foam Type Hair Styling Product", Dec. 15, 1992, pp. 61-69. (with English translation).
Test Report 4 (with English translation), dated Jun. 24, 2011, in regard to Heisei 23 year (Yo) No. 22009.
Test Report dated May 1, 2012, Hoyu Co, Ltd, Product Development Laboratory of General Research & Development Institute, Section Chief: Ryouji Ishikawa, served on May 11, 2012 in regard to No. 5260, 2012 (wa) with English translation, (13 pp).
Third Party Observation issued on May 3, 2011, in corresponding European Application No. 04 009 836.
Third-Party Observation filed on Apr. 27, 2011, in European Patent Application No. 0 400 9836 0 (including translation of submission).
Third-Party Observation filed on Dec. 19, 2009 in European Patent application No. 0 400 9836 0.

Third-Party Observation filed on May 10, 2010 in European Patent application No. 0 400 9836 0.
Third-Party Observation submitted Jun. 24, 2011, in European Patent Application No. 10172766 7.
Third-Party Observation submitted Jun. 24, 2011, in European Patent Application No. 10183376 2.
Third-Party Observation submitted Jun. 3, 2011, in European Patent Application No. 10172766 7, filed Apr. 26, 2004.
Third-Party Observation submitted May 12, 2011, in European Patent Application No. 04009836 0.
Third-Party Observation submitted May 3, 2011, in European Patent Application No. 0 400 9836 0.
Unichemy Corp. Experimental Report, in regard to No. 22056, 2011, (yo), Issued on Jun. 24, 2011 (with English translation).
Vivid Highlight, Iriya Cosmetics, Packaging and Instructions Insert, Sep. 6, 1996, (with English translation).
Written Demand for Appeal filed Sep. 10, 2010, in Japanese application No. 2004-130373 (w/ English Translation).
Yamagata, Yoshifumi, et al. Fragrance Journal "Science of Foam: Function and Physical Properties of Foam " Dec. 15, 1992 pp. 37-47 (with English translation).
Yamakawa, Arata, et al., Fragrance Journal, "Development and Objective of Mousse Hair Cosmetic Products", Dec. 15, 1992, pp. 48-54. (with English translation).
Notification of Third Office Action Chinese Application No. 200780100733.0 dated Oct. 9, 2012.

* cited by examiner

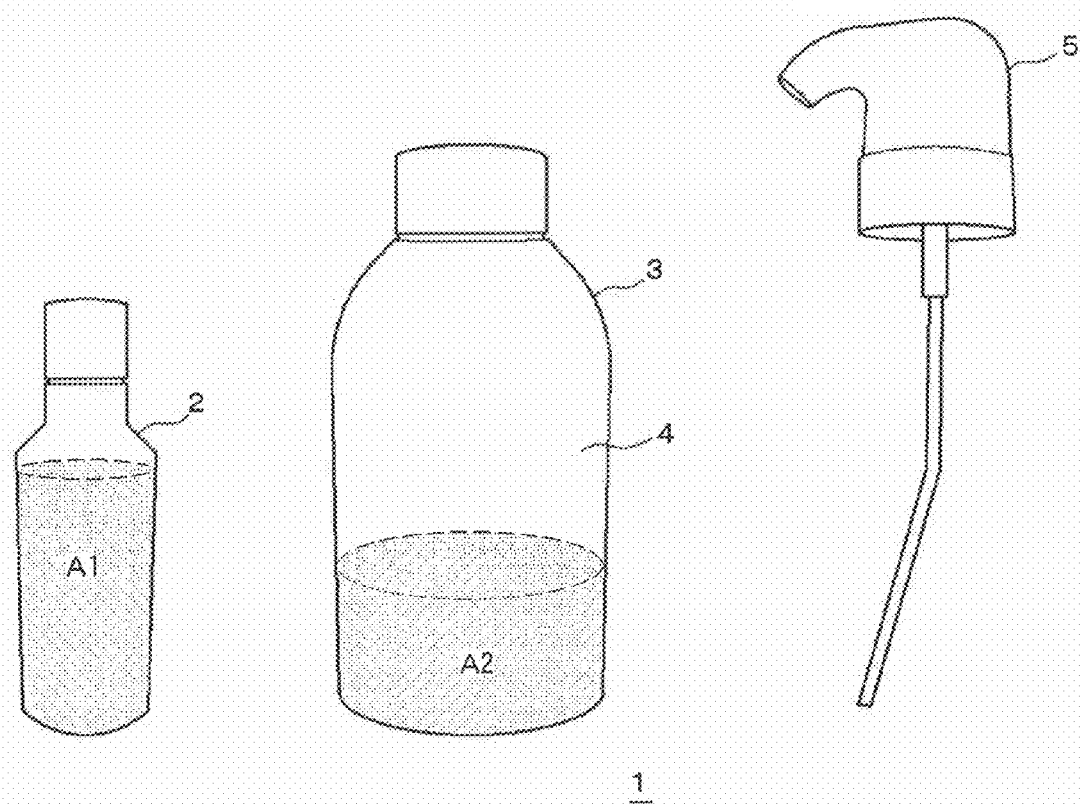

(a)

(b)

X—X Cross-section (a)

(b)

TWO-PART HAIR DYE OR BLEACH COMPOSITION

TECHNICAL FIELD

The present invention relates to a two-part hair cosmetic for hair dyeing or bleaching which includes first and second agents of which a two-part hair dye or bleach composition is constituted and a squeeze container filled with a mixed solution thereof.

BACKGROUND ART

Examples of discharge containers containing liquid contents and discharging such contents therefrom include a squeeze container. Squeeze containers can be classified as squeeze containers provided with a nozzle cap, squeeze containers provided with a squeeze foamer and the like, according to the kind of cap attached to the container body.

To complete a product using such a squeeze container, it is necessary to select from among various kinds of materials, shapes and the like depending on the physical properties of the contents and the intended use and the like, and then draw up a design based on the discharge amount per one discharge, the discharge mode, i.e., whether the contents are discharged as a liquid or a foam, the discharge frequency and the like. Such selection and design requires a large amount of work and in new product development often entails great difficulties, even if carried out with the cooperation of people skilled in the art of containers and in the art of the contents.

For example, a face wash cosmetic is used approximately several times per day in an amount of about 1 g each time. Thus, the conditions required for a container containing a face wash cosmetic are that it can be left for a period of several months to several years with its contents inside, and the discharge mode can be a liquid or in a fine foam. Accordingly, it is necessary to select the optimum materials for those conditions and draw up a design based thereon.

On the other hand, two-part hair dye or bleach compositions are constituted of a first agent containing an alkaline agent and a second agent containing hydrogen peroxide. Such compositions have to be used by thoroughly mixing the first and second agents just before use. In addition, all of the composition needs to be used up immediately after mixing. Furthermore, a mixed solution of the first and second agents has to be applied on the hair and then left for about 30 minutes, during which time the mixed solution must not drip. Therefore, to apply the mixed solution on the hair in a liquid state as is, the mixed solution needs to be in the form of a gel or a cream having a viscosity of at least several thousand mPa·s. Considering the ease of applying on the hair and problems such as corrosion of the container by the composition, a squeeze container provided with a nozzle cap is generally used for containing such a form of a two-part hair dye or bleach composition.

However, to carry out dyeing or bleaching without any unevenness using a gel- or cream-formed two-part hair dye or bleach composition, since the mixed solution has a high viscosity as mentioned above, not only skill is required, but the hair must be "pre-blocked" (braiding the hair into sections at the front, sides and rear of the head). Thus, a lot of time and effort is required to carry out such dyeing or bleaching.

In recent years, to resolve this problem, two-part hair dye or bleach compositions have been proposed which contain a foaming agent in at least one of the first or second agents (Patent Documents 1 and 2). If the mixed solution of these first and second agents is applied on the hair by discharging it in a foam by a foamer container, dyeing or bleaching can be carried out simply without any trouble.

Patent Document 1: JP-A-2004-339216
Patent Document 2: JP-A-2006-124279

DISCLOSURE OF THE INVENTION

Problems to be Solved by the Invention

Patent Documents 1 and 2 disclose known pump foamer containers, squeeze containers and the like as foamer containers which discharge in a foam a mixed solution of first and second agents of a two-agent type composition for hair dyeing or bleaching.

However, there is a need for further investigation into a foamer container which is capable of smoothly repeating the discharge operation of a mixed solution of first and second agents, which does not allow dripping even if a foamy mixed solution is left for about 30 minutes after being applied on the hair, and yet which can carry out dyeing or bleaching without any unevenness.

Means for Solving the Problems

The present inventors discovered that when discharging a mixed solution of first and second agents of a two-part hair dye or bleach composition in a foam from a squeeze container, factors such as the ratio between the liquid amount of the mixed solution filled in the squeeze container and the inner volume of the container body, and the cross-sectional profile and cross-sectional area of the container body, have a large effect on foam quality. Furthermore, the present inventors discovered that foam quality could be controlled by setting these factors in specific ranges, and that dyeing or bleaching could even be carried out without any drips or color unevenness. As a result of this discovery, the present inventors completed the present invention.

Specifically, a first aspect of the present invention provides a two-part hair cosmetic for hair dyeing or bleaching which includes a two-part hair dye or bleach composition having a first agent containing an alkaline agent and a second agent containing hydrogen peroxide, and a squeeze container for discharging in a foam a mixed solution of the first and second agents, wherein at least one of the first or second agents contains a foaming agent, the mixed solution of the first and second agents has a viscosity (25° C.) of from 1 mPa·s to 100 mPa·s, the squeeze container has a container body and a squeeze foamer, the squeeze foamer has a gas-liquid mixing chamber for causing the mixed solution to foam by mixing air in the container body with the mixed solution, foam homogenizing means for homogenizing foam of the mixed solution which has been made to foam in the gas-liquid mixing chamber, and a discharge outlet for discharging the homogenized foam, and a ratio between a total volume of the first and second agents and an inner volume of the container body (total volume/inner volume) is in the range of from 0.30 to 0.60.

A second aspect of the present invention provides a two-part hair cosmetic for hair dyeing or bleaching which includes a two-part hair dye or bleach composition having a first agent containing an alkaline agent and a second agent containing hydrogen peroxide and a squeeze container for discharging in a foam a mixed solution of the first and second agents, wherein at least one of the first or second agents contains a foaming agent, the mixed solution of the first and second agents has a viscosity (25° C.) of from 1 mPa·s to 100 mPa·s, the squeeze container has a container body and a squeeze foamer, the squeeze foamer has a gas-liquid mixing chamber for causing the mixed solution to foam by mixing air in the container body with the mixed solution, foam homogenizing means for homogenizing foam of the mixed solution which has been made to foam in the gas-liquid mixing chamber, and a discharge outlet for discharging the homogenized foam, a ratio between a total volume of the first and second agents and an inner volume of the container body (total volume/inner volume) is in the range of from 0.30 to 0.70, and a torso outer shape of the container body has a cross-section with a ratio of minor axis to major axis at a middle portion in a height direction of the container body of from 0.50 to 1.0.

A third aspect of the present invention provides a two-part hair cosmetic for hair dyeing or bleaching which includes a two-part hair dye to bleach composition having a first agent containing an alkaline agent and a second agent containing hydrogen peroxide and a squeeze container for discharging in a foam a mixed solution of the first and second agents, wherein at least one of the first or second agents contains a foaming agent, the mixed solution of the first and second agents has a viscosity (25° C.) of from 1 mPa·s to 100 mPa·s, the squeeze container has a container body and a squeeze foamer, the squeeze foamer has a gas-liquid mixing chamber for causing the mixed solution to foam by mixing air in the container body with the mixed solution, foam homogenizing means for homogenizing foam of the mixed solution which has been made to foam in the gas-liquid mixing chamber, and a discharge outlet for discharging the homogenized foam, a ratio between a total volume of the first and second agents and an inner volume of the container body (total volume/inner volume) is in the range of from 0.30 to 0.70, and a torso outer shape of the container body has a cross-section with an area at a middle portion in a height direction of the container body of from 12 cm² to 30 cm².

Effect of the Invention

According to the first aspect of the present invention, the mixed solution of the first and second agents includes a foaming agent and has a specific viscosity; a squeeze container provided with a specific squeeze foamer is used; and the ratio between the total volume of the first and second agents and the inner volume of the container body (total volume/inner volume) is in the range of from 0.30 to 0.60. As a result, the foam quality of the mixed solution when repeated squeezing is carried out can be made very fine from start to finish of the squeezing; and an excellent hair dyeing performance can be achieved, such as the enablement of dyeing or bleaching without any drips or unevenness. Furthermore, the number of squeeze repetitions from start to finish of the squeezing corresponding to the required total discharge amount on the hair can be reduced by discharging approximately 3 g or more of foam, which is suitable to be taken on one hand, in a single squeeze. Therefore, the hand can be prevented from becoming tired even when applying foam of the mixed solution over all of the hair.

According to the second aspect of the present invention, the same mixed solution and squeeze foamer as in the first aspect of the present invention are used; and a torso outer shape of the container body has a cross-section with a ratio of minor axis to major axis at a middle portion in a height direction of the container body of from 0.50 to 1.0. As a result, the foam quality of the mixed solution discharged from the squeeze container can be made finer, and an excellent hair dyeing performance can be achieved, such as the enablement of dyeing or bleaching without any drips or unevenness. Furthermore, approximately 3 g or more of foam, which is suitable to be taken on one hand, in a single squeeze, can be discharged, and the recovery properties of the squeezed container can be improved. Therefore, it is easier to carry out repeated squeezing continuously with a stable foam quality.

According to the third aspect of the present invention, the same mixed solution and squeeze foamer as in the first aspect of the present invention are provided; and a torso outer shape of the container body has a cross-section with an area at a middle portion in a height direction of the container body of from 12 cm² to 30 cm². As a result, the foam quality of the mixed solution discharged from the squeeze container can be made finer, and an excellent hair dyeing performance can be achieved, such as the enablement of dyeing or bleaching without any drips or unevenness. Furthermore, it is easier to grip the container body, easy to increase the amount discharged from a single squeeze, and easy to discharge approximately 3 g or more of foam, which is suitable to be taken on one hand in a single squeeze. Therefore, the hand can be prevented from becoming tired even when applying foam of the mixed solution over all of the hair.

BRIEF DESCRIPTION OF THE DRAWINGS

FIG. 1A is a schematic view of the two-part cosmetic for hair dyeing or bleaching of the first aspect of the present invention prior to the mixing of the first and second agents;

Figure 1B:
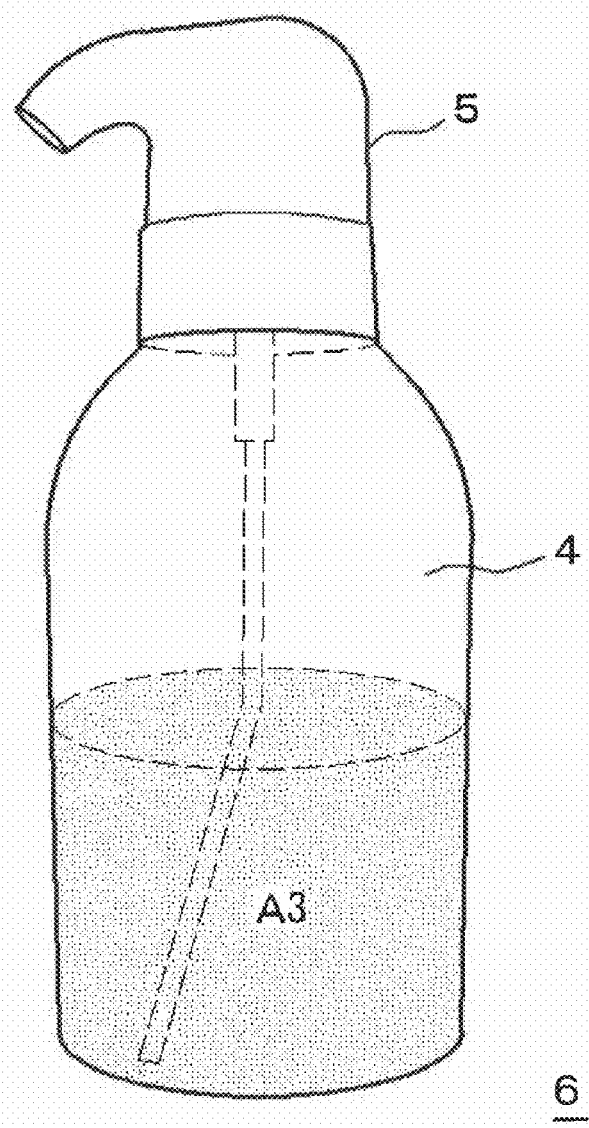
FIG. 1B is a schematic view of the two-part hair cosmetic for hair dyeing or bleaching of the first aspect of the present invention after the first and second agents have been mixed.

| DESCRIPTION OF THE REFERENCE NUMERALS | |
| --- | --- |
| 1 | two-part hair cosmetic for hair dyeing or bleaching |
| 2 | first container |
| 3 | second container |
| 4 | container body of second container or container body of squeeze container |
| 5 | squeeze foamer |
| 6, 6B | squeeze container |
| 7 | cap member |
| 8 | head member |
| 10 | mixing device |

-continued

DESCRIPTION OF THE
REFERENCE NUMERALS

| 11 | gas-liquid mixing chamber |
| 12 | air induct path |
| 13 | dip tube |
| 14 | foam homogenizing means |
| 15 | liquid path |
| 16 | liquid path |
| 17 | discharge outlet |
| 18 | foam homogenizing means |
| 19 | gap |
| 20 | check valve |
| 21 | discharge nozzle |
| A1 | first agent |
| A2 | second agent |
| A3 | mixed solution |
| La | minor axis |
| Lb | major axis |
| Lx | axis perpendicular to aperture face of discharge outlet |
| Ly | vertical direction |
| S | cross-section of container body |

MODE FOR CARRYING OUT THE INVENTION

The present invention will now be described in more detail while referring to the drawings. It is noted that in the drawings, like reference numerals represent the same or similar structural elements.

FIG. 1A is a schematic view showing one embodiment of the two-part hair cosmetic for hair dyeing or bleaching of the first aspect of the present invention and illustrating the state prior to the mixing of the first and second agents. FIG. 1B illustrates the state after the first and second agents have been mixed.

As illustrated in FIG. 1A, this two-part hair cosmetic 1 for hair dyeing or bleaching includes a first agent A1 filled in a first container 2, a second agent A2 filled in a second container 3, and a squeeze foamer 5. The container body 4 of the second container 3 also serves as the container body of the squeeze container. As illustrated in FIG. 1B, a squeeze container 6 is constituted of the container body 4 and the squeeze foamer 5. Here, the squeeze container is preferably such a container as causes a mixed solution to foam by mixing the mixed solution with air in the same container body. Examples of such a squeeze container include a container like the squeeze container 6 illustrated in FIG. 1B, which discharges its contents while in an upright manner (for example, "S1 Squeeze Foamer", manufactured by Daiwa Can Company). Further examples include a container such as the squeeze container 6B illustrated in FIG. 7, which is provided with a check valve (not shown) in the discharge path of the liquid so that it can discharge its contents either in an upright or inverted manner, since when the container is standing upright the portion which is the air induct path becomes the liquid induct path when inverted, while the dip tube which is the liquid induct path when the container is standing upright becomes the air induct path when inverted (for example, "Squeeze Foamer RF-270" manufactured by Toyo Seikan Kaisha, Ltd.). From the perspective of the discharge performance of the foam, a squeeze container which can discharge its contents in an upright manner like as illustrated in FIG. 1B is preferred.

The concept of the "two-pair hair dye or bleach composition" in the present invention includes hair dye or bleach compositions which contain a first agent and a second agent and which are used by mixing these agents at the time of use. In the case of a hair dye composition, the first agent A1 contains an alkaline agent and a dye, and the second agent A2 contains hydrogen peroxide. Furthermore, in the case of a hair bleach composition, the first agent A1 contains an alkaline agent but not a dye, and the second agent A2 contains hydrogen peroxide. In addition, in the case of hair dye compositions as well as hair bleach compositions, this concept also includes embodiments wherein a third agent containing a persulfate is used. In such a case, the first, second, and third agents are used by mixing them together.

The hair cosmetic 1 for hair dyeing or bleaching of the first aspect of the present invention includes a foaming agent in at least one of the first agent A1 or the second agent A2 of the two-part hair dye or bleach composition, with the mixed solution A3 being adjusted to have a certain viscosity, wherein a specific container is used as the squeeze container 6, and a specific ratio between the initial filled amount of the mixed solution A3 and the inner volume of the container body 4 is set. As a result, the foam quality and discharge properties of the mixed solution A3 discharged in a foam from the squeeze container are improved from start to finish of the squeezing.

Here, as the alkaline agent contained in the first agent A1, ammonia, an alkanolamine such as monoethanolamine, sodium hydroxide, and potassium hydroxide can be used. Furthermore, a buffer may be appropriately added, for example, an ammonium salt such as ammonium hydrogencarbonate and ammonium chloride, and a carbonate such as potassium carbonate and sodium hydrogencarbonate.

The concentration of the alkaline agent can be appropriately set so that the pH in the mixed solution A3 of the first agent A1 and the second agent A2 is from 8 to 12, and preferably from 9 to 11.

On the other hand, the concentration of the hydrogen peroxide in the second agent A2 is preferably in the range of from 1 mass % to 9 mass %, and more preferably in the range of from 3 mass % to 6 mass %. The hydrogen peroxide concentration in the mixed solution of the first agent A1 and the second agent A2 is preferably in the range of from 1 mass % to 6 mass %, and more preferably in the range of from 2 mass % to 5 mass %. Furthermore, to suppress decomposition of the hydrogen peroxide, the pH of the second agent A2 is preferably in the range of from 2 to 6, and more preferably in the range of from 2.5 to 4.

Both the first agent A1 and the second agent A2 preferably have water as their main solvent.

At least one of the first agent A1 or the second agent A2 used in the present invention contains a foaming agent. This enables the mixed solution A3 of the first agent A1 and the second agent A2 to easily foam by discharging the mixed solution A3 from the squeeze container 6. Furthermore, the produced foam has a longer life. Although the foaming agent may be anything so long as it has foaming properties, a surfactant is preferable. Examples of the surfactant include nonionic surfactants, anionic surfactants, cationic surfactants, ampholytic surfactants, semipolar surfactants, and the like. Among these, the use of an anionic surfactant is preferred, and using together with an ampholytic surfactant as well is more preferred. Examples of the anionic surfactant include an alkylsulfate, polyoxyethylenealkylethersulfate and the like. Examples of the ampholytic surfactant which can be used include fatty acid amidopropyl betaine, alkyldimethylamine oxide, alkylcarboxymethyl hydroxyethyl imidazolinium betaine, alkyldimethylaminoacetic acid betaine and sulfobetaine.

Furthermore, generally, considering that the first agent A1 in many cases contains ammonia or a carbonate and has a high ionic strength, to solubilize the dye or to improve the sense of feel, the first agent A1 preferably contains a nonionic surfactant, such as a polyoxyethylenealkylether, an alkylpolyglucoside, and an alkylalkanolamide. Among these, an alkylpolyglucoside or polyoxyethylenealkylether are preferred. More specifically, preferred examples of the alkylpolyglucoside have 8 to 14 carbon atoms on the alkyl group and an average degree of condensation of the glucoside of 1 to 2. Furthermore, preferred examples of the polyoxyethylenealkylether have 10 to 18 carbon atoms on the alkyl group and an average degree of polymerization of the polyoxyethylene of 5 to 40.

Furthermore, the second agent A2 may also contain a nonionic surfactant, such as a polyoxyethylenealkylether, an alkylpolyglucoside, and an alkylalkanolamide, and a cationic surfactant, such as alkyltrimethylammonium chloride and dialkyldimethylammonium chloride in order to improve the sense of feel.

If the two-part hair dye or bleach composition is for hair dyeing, the dye contained in the first agent A1 may be an oxidation dye or a direct dye. Examples of the oxidation dye include: dye precursors, such as para-phenylenediamine, para-aminophenol, toluene-2,5-diamine, N,N-bis(2-hydroxyethyl)para-phenylenediamine, 2-(2-hydroxyethyl)para-phenylenediamine, 4-amino-3-methylphenol, 6-amino-3-methylphenol, ortho-aminophenol and 1-hydroxyethyl-4,5-diaminopyrazole; couplers, such as resorcin, 2-methylresorcin, meta-aminophenol, para-amino-ortho-cresol, 5-(2-hydroxyethylamino)-2-methylphenol, meta-phenylenediamine, 2,4-diaminophenoxyethanol, and 1-naphthol; and the like. Examples of the direct dye include para-nitro-ortho-phenylenediamine, para-nitro-meta-phenylenediamine, basic yellow 87, basic orange 31, basic red 12, basic red 51, basic blue 99, acid orange 7, and the like.

It is preferred that at least one of the first agent A1 or the second agent A2 contains a higher alcohol, since this improves the life of the foam of the mixed solution discharged from the squeeze container 6, and suppresses drips from forming when the foam collapses after being applied on the hair. The higher alcohol preferably has 14 to 24 carbon atoms. Examples thereof include myristyl alcohol, cetyl alcohol, stearyl alcohol, behenyl alcohol, isostearyl alcohol, oleyl alcohol, and the like. These can be used as a combination of two kinds or more. Furthermore, these can be contained, based on the whole composition for hair dyeing after the first and second agents have been mixed, in an amount of 0.01 mass % to 3 mass %, preferably 0.1 mass % to 2 mass %, more preferably 0.2 mass % to 1 mass % and even more preferably 0.3 mass % to 0.8 mass %.

In addition, the first agent A1 and the second agent A2 may contain various additives as required. For example, to prevent the scalp from being irritated by an irritant component, such as hydrogen peroxide, which becomes more concentrated due to moisture evaporation after the mixed solution A3 of the first agent A1 and the second agent A2 is applied on the hair, addition of a nonvolatile, hydrophilic solvent, such as a polyol or lower alkyl ether thereof thereto are preferred. Furthermore, to give a conditioning effect to the hair, an ampholytic or cationic polymer, or a silicone and the like are also preferably added. Also they may appropriately contain a perfume material, an ultraviolet ray absorbent, a metal sequestering agent such as edetic acid, an antiseptic, a germicide such as methyl paraoxybenzoate, a stabilizing agent such as dibutyl-hydroxytoluene, 1-hydroxyethane-1,1-diphosphonic acid and sulfuric acid oxyquinoline, an organic solvent such as ethanol, benzyl alcohol and benzyloxy ethanol, a water-soluble polymer compound such as and hydroxyethylcellulose, a moisturizer, and the like.

Furthermore, the viscosity (25° C.) of the first agent A1 is preferably in the range of from 1 mPa·s to 50 mPa·s, more preferably in the range of from 3 mPa·s to 40 mPa·s, and even more preferably in the range of from 5 mPa·s to 30 mPa·s. The viscosity (25° C.) of the second agent A2 is preferably in the range of from 1 mPa·s to 300 mPa·s, more preferably in the range of from 3 mPa·s to 200 mPa·s, and even more preferably in the range of from 5 mPa·s to 100 mPa·s. The viscosity (25° C.) of the mixed solution A3 of the first agent A1 and the second agent A2 is in the range of from 1 mPa·s to 100 mPa·s, preferably in the range of from 3 mPa·s to 50 mPa·s, and more preferably in the range of from 5 mPa·s to 30 mPa·s. It is noted that these viscosity values are found using a B-type rotary viscometer (Model TV-10) with the No. 1 rotor manufactured by Tokimec Inc., after rotating the rotor for 1 minute. Measurement is carried out at a rotation speed of 60 rpm when the measuring target has a viscosity of 100 mPa·s or less, 30 rpm when the measuring target has a viscosity of from 100 mPa·s to 200 mPa·s, and 12 rpm when the measuring target has a viscosity of 200 mPa·s to 500 mPa·s. The viscosities of the first agent, second agent and mixed solution are taken as the values measured in a 25° C. thermostat bath. Furthermore, in the case of the mixed solution, the value measured immediately after mixing is used, and any temperature change due to heat of reaction is ignored. By setting the viscosity of the mixed solution in the above range, the mixed solution can be homogenously mixed without producing a foam in the container body. Furthermore, homogenous foam discharged from the squeeze foamer can be obtained which are easily applied on the hair, react well with the hair, and which do not easily form drips after being applied on the hair.

Adjustment of the viscosities of the first agent A1, second agent A2 and their mixed solution A3 to within the above ranges can be carried out by adding a water-soluble solvent such as ethanol to the first agent A1 and the second agent A2, or by appropriately adjusting the kind or added amount of the above-described surfactant, polyol or higher alcohol.

Figure 2:
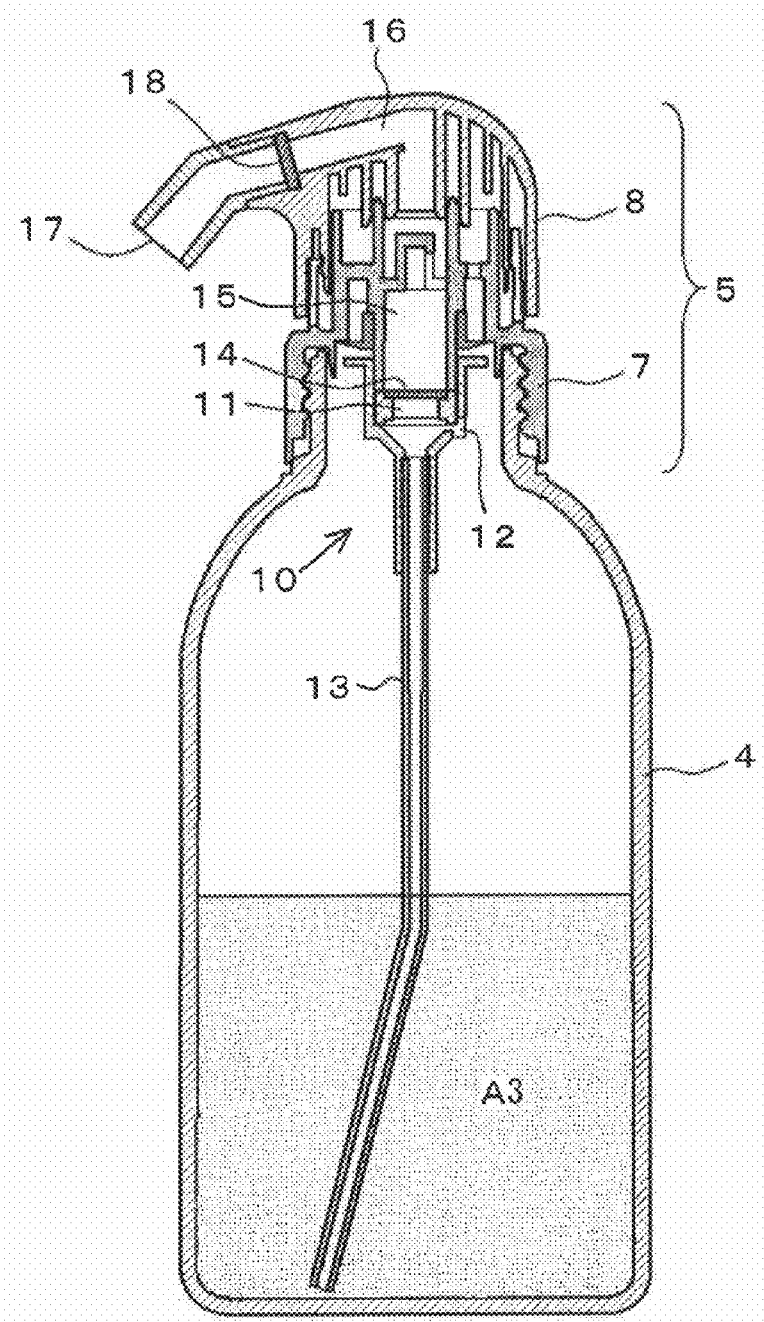
FIG. 2 is a cross-sectional view of a squeeze container.

Further, the squeeze container 6 for causing the two-part hair dye or bleach composition to foam has the same basic structure as a known squeeze container disclosed in, for example, JP-A-1995-215352. As illustrated in FIG. 2, the squeeze container 6 is composed of a flexible container body 4 and a squeeze foamer 5. The squeeze foamer 5 is composed of a cap member 7 attached to an aperture of the container body 4, and a head member 8 which sits over the cap member 7.

A mixing device 10 is fitted to the cap member 7 so as to hang down from the cap member 7. In the interior of the mixing device 10 are provided a gas-liquid mixing chamber 11, and an air induct path 12 through which the interior space in the container body 4 and the gas-liquid mixing chamber 11 are in communication with each other. Furthermore, in the mixing device 10, a dip tube 13 is fitted which extends into the container body 4. A net is attached to the ceiling of the gas-liquid mixing chamber 11 as foam homogenizing means 14, and the head member 8 side of the foam homogenizing means 14 serves as a liquid path 15.

On the other hand, on the head member 8 are provided a liquid path 16 connecting to the liquid path 15 of the cap member 7, and a discharge outlet 17 connecting to the liquid path 16. Furthermore, a net is provided in the liquid path 16 in the vicinity of the discharge outlet 17 as foam homogenizing means 18.

In the present invention, the foam homogenizing means 14 and 18 of the gas-liquid mixing chamber and the discharge outlet are not limited to a net. A porous material such as a sponge or a sintered body may also be used.

One method for using such a two-part hair cosmetic 1 for hair dyeing or bleaching is to, during use, first transfer the whole amount of the first agent A1 filled in the first container 2 to the container body 4 of the second container 3 filled with the second agent A2 to prepare the mixed solution A3. Accordingly, the total volume of the first and second agents becomes the initial filled amount of the mixed solution A3 in the container body 4. In the present invention, this mixing is carried out so that the mixing of the first agent A1 and the second agent A2 produces as little foam as possible, or so that no foam are produced. Here, "not producing foam" or "no foam is produced" are a concept which excludes the intentional production of foam, but includes cases where a small amount of foam is unintentionally produced when the mixing is carried out like in the specific examples illustrated below. As long as a foam is not produced during the mixing, there are no restrictions on the mixing method. Examples of such methods include mixing carried out by shaking a test tube, or by moving the container body 4 from a roughly upright state to an inverted through sideways state, and then once again returning to a roughly upright state. More specifically, the lid of the second container 3 is put on the container body 4 containing the first agent A1 and the second agent A2, and the cycle of moving the container body 4 from a roughly upright state to an inverted through sideways state, and then once again returning to a roughly upright state, may be carried out 1 to 30 times, preferably 1.5 to 20 times, and more preferably 2 to 10 times, in 10 seconds. The operation of moving from a roughly upright state to an inverted though sideways state, and then once again returning to a roughly upright state is carried out 1 to 15 times, preferably 2 to 10 times, and even more preferably 3 to 7 times. A uniform mixed solution A3 can be easily obtained without a foam being produced even if the container body 4 is slowly shaken in this manner, since the first agent A1 and the second agent A2 used in the present invention have a much lower viscosity than a gel or cream type agent.

Figure 7:
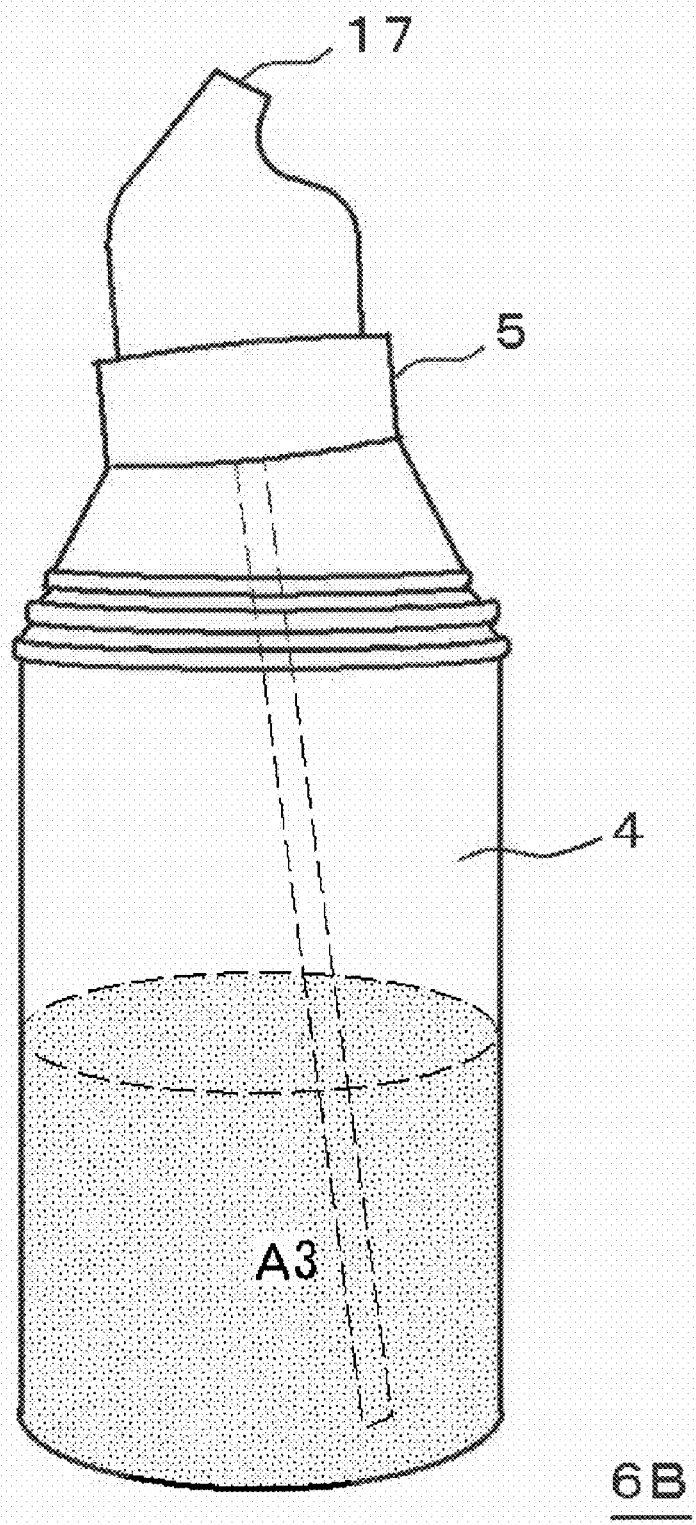
FIG. 7 is a schematic view of the squeeze container after the first and second agents have been mixed.

As illustrated in FIG. 1B or FIG. 7, after the first agent A1 and the second agent A2 have been mixed, the squeeze foamer 5 is attached to the container body 4. It is noted that the mixing of the first agent A1 and the second agent A2 may also be carried out by transferring the whole amount of the first agent A1 to the container body 4 of the second container filled with the second agent A2, then attaching the squeeze foamer 5 to the container body 4 in place of the lid of the second container 3, and slowly shaking the container body 4 by a mixing method like that of shaking a test tube.

The foam of the thus-discharged mixed solution A3 is applied on the hair using a hand or a comb. Furthermore, this discharging is repeated until a required amount has been discharged. Hair dyeing or bleaching can be carried out by subsequently leaving the foam on the hair for a given amount of time and then washing off.

Figure 3:
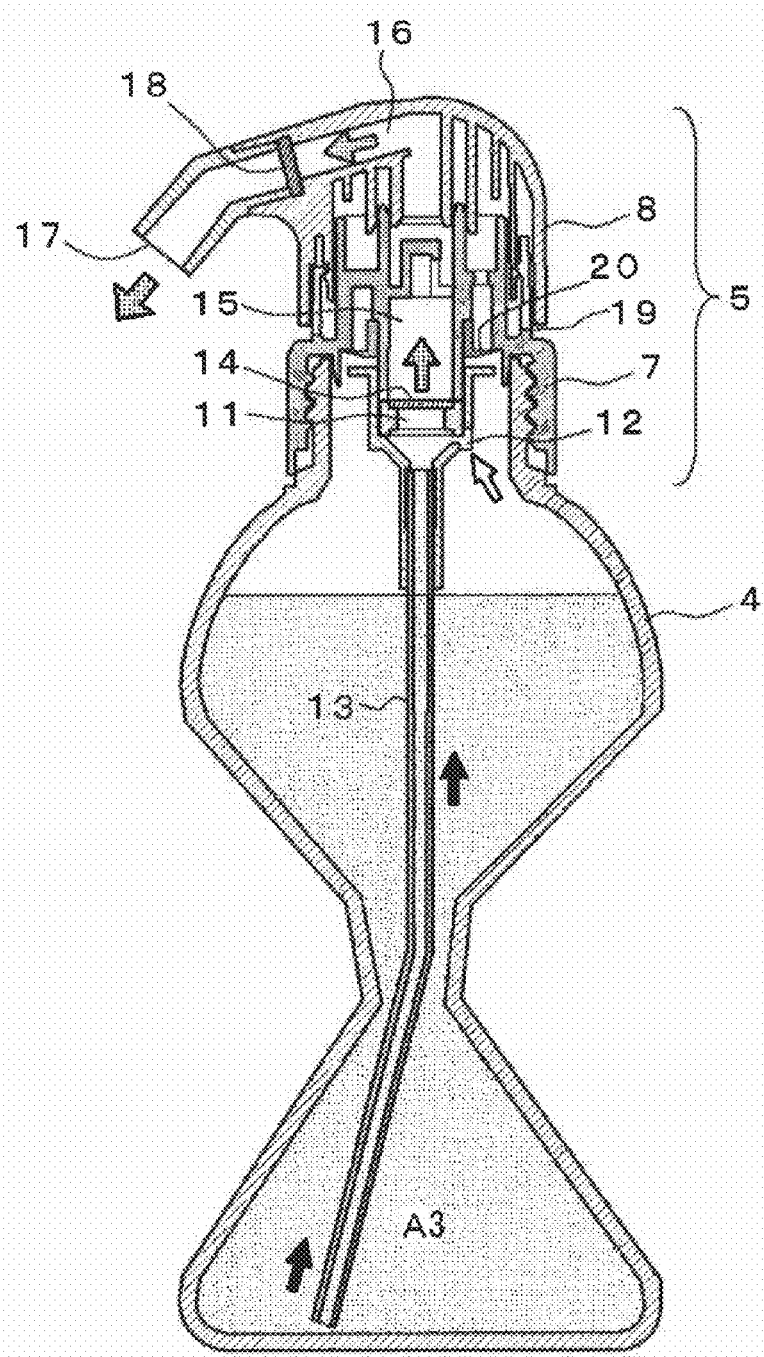
FIG. 3 is a cross-sectional view of the squeeze container when being squeezed.

Here, in the two-part hair cosmetic 1 for hair dyeing or bleaching of the first aspect of the present invention, the ratio between the total volume of the first agent A1 and the second agent A2 (i.e., the initial filled amount of the mixed solution A3; hereinafter the same) and the inner volume of the container body 4 (total volume/inner volume) is characterized by being in the range of from 0.30 to 0.60. Therefore, for example, when the liquid amount of the mixed solution A3 is 100 mL, a container body 4 having an inner volume of 167 to 333 mL is used. This ratio between the initial filled amount of the mixed solution A3 and the inner volume of the container body 4 is preferably in the range of from 0.40 to 0.60, more preferably in the range of from 0.35 to 0.55, even more preferably in the range of from 0.40 to 0.50 and even more preferably in the range of from 0.45 to 0.50. By setting the ratio between the initial filled amount of the mixed solution A3 and the inner volume of the container body 4 in such a specific range, the foam of the mixed solution A3 discharged from the discharge outlet 17 can have a very fine foam quality and better foam life right from the start of squeezing, and drips after the foam have been applied on the hair can be suppressed. More specifically, by setting the ratio between the initial filled amount of the mixed solution A3 and the inner volume of the container body 4 to 0.30 to 0.60, as illustrated in FIG. 3, when discharging the foam the gas-liquid mixing ratio, which acts as an index for foam quality, can be stabilized without the air induct path 12 of the gas-liquid mixing chamber 11 being blocked by mixed solution A3 in the container body 4 from the start of squeezing even if the container body 4 is squeezed until both opposing sides thereof come into contact with each other. Therefore, when applying on the hair, drips are less likely to form and color unevenness is less likely to occur.

This gas-liquid mixing ratio is a value obtained by measuring the mass and volume of the discharged product at 25° C. in the following manner. Specifically, 20 g is discharged from a squeeze container 6 containing 80 g of the mixed solution A3 into a 1,000 mL graduated cylinder. The gas-liquid mixing ratio (mL/g) is found by measuring the total volume of the foam and the liquid 1 minute after the initial discharge, and then dividing the total volume (mL) of the measured foam and liquid by 20 g. However, when measuring the effects of the ratio between the total volume of the first agent A1 and the second agent A2 and the inner volume of the container body 4, the value is found by measuring the initial filled amount.

Figure 4:
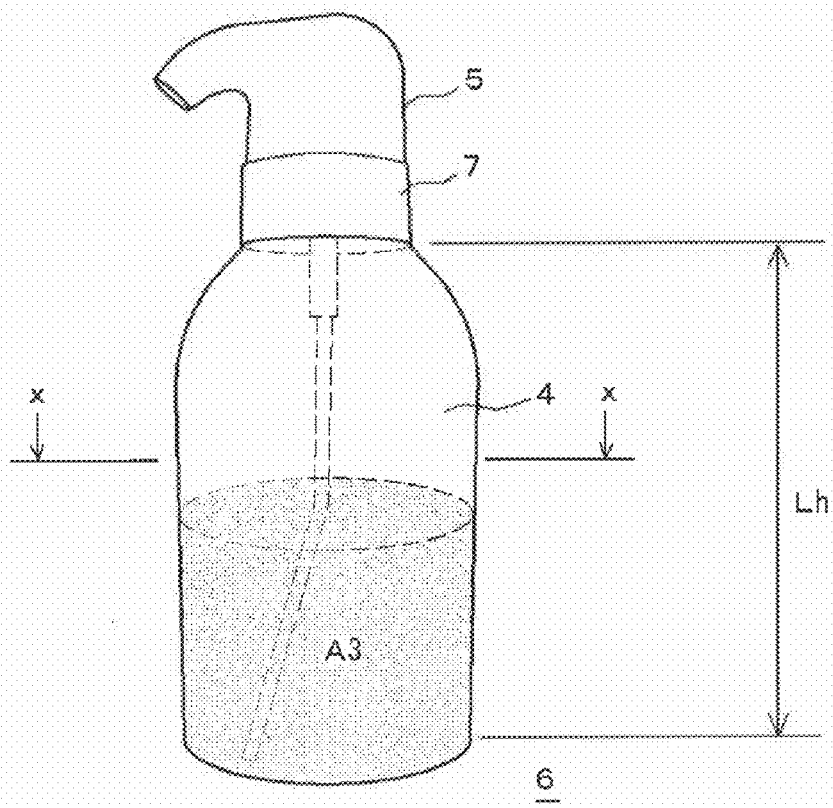
FIG. 4 is an explanatory diagram of the cross-section of the squeeze container.
Figure 4:
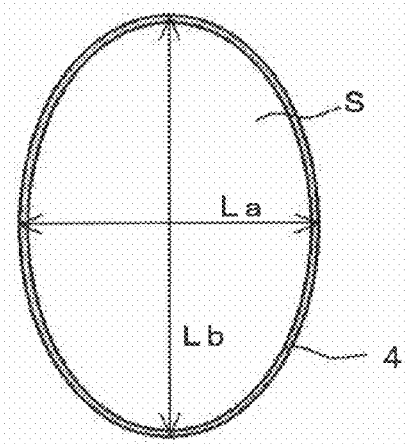

The two-part hair cosmetic for hair dyeing or bleaching of the second aspect of the present invention has, in the two-part hair cosmetic for hair dyeing or bleaching of the first aspect of the present invention, a ratio between the total volume of the first agent A1 and the second agent A2 and the inner volume of the container body 4 (total volume/inner volume) of from 0.30 to 0.70, preferably from 0.35 to 0.60, more preferably from 0.40 to 0.55, and even more preferably from 0.45 to 0.50. Furthermore, as illustrated in FIG. 4, the torso outer shape of the container body 4 has a cross-section S with a ratio a/b of minor axis La to major axis Lb at a middle portion in a height direction of the container body 4 of from 0.5 to 1.0. Here, "middle portion in a height direction of the container body 4" refers to the middle portion of the height Lh (height from the bottom of the container body 4 to the lower edge of a cap member 7 of the squeeze foamer 5) of the container body 4.

The ratio a/b of minor axis La to major axis Lb of the cross-section S is preferably in the range of from 0.60 to 0.90, and more preferably in the range of from 0.70 to 0.80. The cross-section S of the container body 4 is preferably an ellipse rather than a circle.

The ratio a/b of minor axis La to major axis Lb affects the thrust required to squeeze the container body 4 and the liquid amount which is discharged by squeezing. By setting this ratio a/b of minor axis La to major axis Lb to 0.5 to 1.0, a sufficient foam amount can be discharged by squeezing with a smaller thrust without having to squeeze the container body 4 until both opposing sides thereof come into contact with each other. This also allows the recovery properties of the squeezed container body 4 to be improved.

More specifically, when discharging 3 g or more of the mixed solution A3, which is suitable to be taken on one hand, in a single squeeze from the container body 4, the thrust required to squeeze the container body 4 can be set to 5 kgf or less.

Here, the thrust is a value measured in the following manner. Specifically, the thrust is the measured value at 25° C., with a filled amount of mixed solution A3 of 80 g, of the maximum load at which the middle portion of the height Lh (height from the bottom of the container body 4 to the lower edge of a cap member 7 of the squeeze foamer 5) of the container body 4 is squeezed at 15 mm/sec up to a distance ½ of the minor axis in the minor axis direction from both opposing sides of the container body 4 with a rod-like member. This rod-like member is 15 mm in diameter, is made of stainless steel, and has a tip with a height of 5 mm in a roughly dome shape. However, when measuring the effects of the ratio between the total volume of the first agent A1 and the second agent A2 and the inner volume of the container body 4, the value is found by measuring the initial filled amount.

Furthermore, regarding the foam amount discharged by one squeeze, the mixed solution A3 can easily be set to 2 g or more, which is suitable for providing in one hand, and more preferably 3 g or more. Therefore, even when applying the mixed solution over all of the hair, the number of squeezes required to discharge that mixed solution can be set at about 30 times or less, so that the hand doing the squeezing does not get tired. Furthermore, when the discharged foam is applied on the hair, drips are less likely to form and color unevenness is less likely to occur.

The two-part hair cosmetic for hair dyeing or bleaching of the third aspect of the present invention has, in the two-part hair cosmetic for hair dyeing or bleaching of the first aspect of the present invention, a ratio between the total volume of the first agent A1 and the second agent A2 and the inner volume of the container body (total volume/inner volume) of from 0.30 to 0.70, preferably from 0.35 to 0.60, more preferably from 0.40 to 0.55, and even more preferably from 0.45 to 0.50. Furthermore, the torso outer shape of the container body 4 has an area at a middle portion in a height direction of the container body 4 of from 12 $cm^2$ to 30 $cm^2$, preferably from 17 $cm^2$ to 25 $cm^2$, and more preferably from 19 $cm^2$ to 23 $cm^2$.

The area of the cross-section S affects how easily the container body 4 is to grip, the thrust required to squeeze the container body 4, and the liquid amount which is discharged by squeezing. Thus, by setting this area in the above-described range, the liquid amount of the mixed solution A3 discharged by one squeeze can easily be set to 2 g or more, and more preferably 3 g or more, without having to squeeze the container body 4 until both opposing sides thereof come into contact with each other.

Therefore, even when applying the mixed solution over all of the hair, the number of squeezes required to discharge that mixed solution can be set at about 30 times or less, so that the hand doing the squeezing does not get tired. Furthermore, when the discharged foam is applied on the hair, drips are less likely to form and color unevenness is less likely to occur.

The compositions of the two-part hair cosmetic for hair dyeing or bleaching of the above first, second and third aspects of the present invention may be appropriately combined.

Furthermore, in all of the first, second and third two-part hair cosmetics for hair dyeing or bleaching, to reduce the thrust required to squeeze the container body 4 and to improve the recovery properties of the squeezed container body 4, the container body 4 is preferably formed from a polyolefin resin, such as polypropylene (PP), high density polyethylene (HDPE), medium density polyethylene (MDPE), low density polyethylene (LDPE) and linear low density polyethylene (LLDPE). Among them, polypropylene (PP) is preferable. Furthermore, in the case of forming the container body 4 from such a polyolefin resin, the "⅔ power coefficient", which is the ratio between the resin weight w (g) of the container body 4 and the ⅔ power of the inner volume V of the container body 4 ($w/V^{2/3}$), is preferably set at a range of from 0.40 to 0.60, and more preferably at a range of from 0.45 to 0.55. Thus, if the inner volume of the container body 4 is 210 mL, the resin weight is preferably in the range of from 14 g to 20 g, and more preferably in the range of from 16 g to 18 g. As a result, the thrust required for squeezing can be reduced, recovery properties can be improved, and continuous squeezing can be repeatedly carried out.

In addition, in all of the first, second and third two-part hair cosmetics for hair dyeing or bleaching, to even further improve the foam quality of the foam of the mixed solution A3 discharged from the squeeze container 6, it is preferred to set the ratio between the aperture area of the narrowest portion of the air induct path 12 and the flow path cross-sectional area of the dip tube 13 (aperture area of the narrowest portion/flow path cross-sectional area) to from 0.05 to 0.25, more preferably from 0.055 to 0.20, and even more preferably from 0.060 to 0.10. If a plurality of air induct paths 12 of the squeeze foamer 5 are formed, the ratio between the total of those aperture areas of the narrowest portions and the flow path cross-sectional area of the dip tube 13 is set in the above range. From the perspectives of ease of molding and foam quality, the number of air induct paths 12 is preferably in the range of from 1 to 8, more preferably in the range of from 2 to 6 and even more preferably 3 or 4. Furthermore, if there are variations in the cross-sectional area of the dip tube 13 flow path, the flow path cross-sectional area of the narrowest portion is used in the calculation of the above ratio.

As a result of the above features, the gas-liquid mixing ratio is reduced and the proportion of liquid in the foam is increased, whereby the tendency of drips to form can be prevented. Furthermore, deterioration in dyeing performance, such as a reduction in the application efficiency of the mixed solution A3 on the hair (liquor ratio) caused by individual bubbles becoming larger and turning into foam having a rough texture, so-called "crab bubbles", due to the gas-liquid mixing ratio becoming too high, and even dripping or color unevenness, can be prevented.

In addition, the roughness of the net forming the foam homogenizing means 14 on the gas-liquid mixing chamber 11 side is preferably a 50 to 220 mesh, more preferably a 90 to 195 mesh, and even more preferably a 130 to 170 mesh. The roughness of the net forming the foam homogenizing means 18 on the discharge outlet 17 side is preferably a 150 to 280 mesh, more preferably a 165 to 250 mesh, and even more preferably a 180 to 220 mesh. Here, "mesh" refers to the number of holes per 1 inch.

Figure 5:
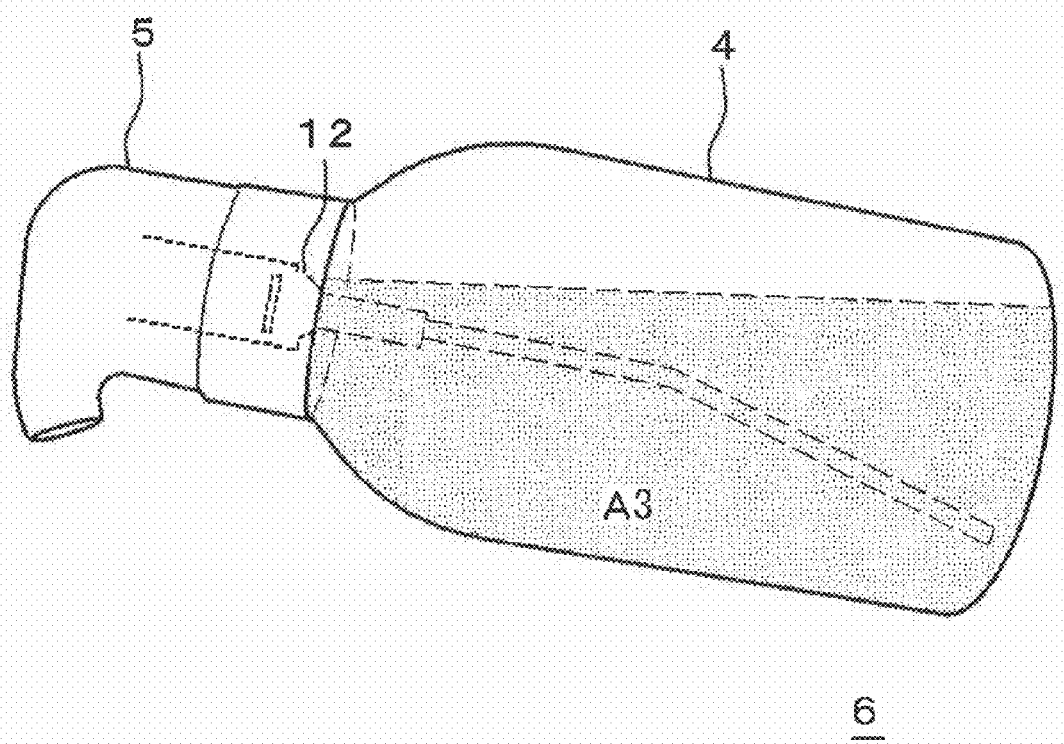
FIG. 5 is a schematic view of the squeeze container in an inclined state.

Furthermore, as illustrated in FIG. 5, if a user excessively tilts the squeeze container 6 upon discharging the mixed solution A3 as foam, so that the mixed solution A3 in the container body 4 blocks the air induct path 12 of the squeeze foamer 5, the mixed solution A3 cannot be discharged in a foam even if the container body 4 is squeezed. Therefore, a container structure which does not allow the squeeze container 6 to be tilted in this way when being squeezed by a user is preferable.

Figure 6:
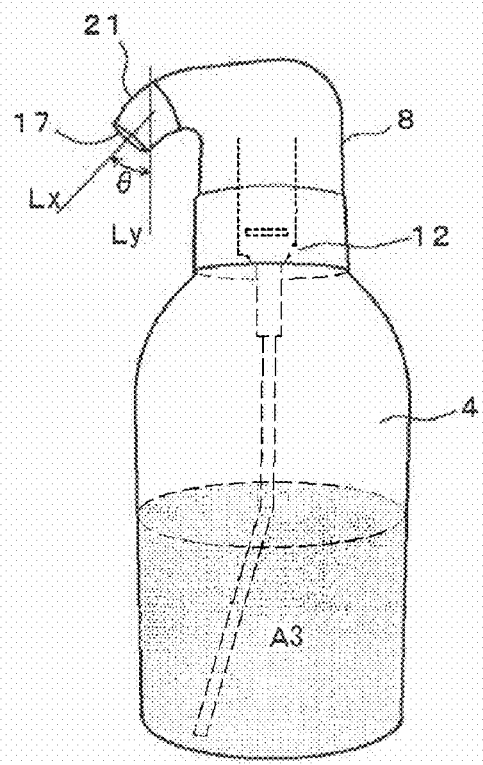
FIG. 6 is an explanatory diagram of the two-part cosmetic for hair dyeing or bleaching provided with a nozzle.
Figure 6:
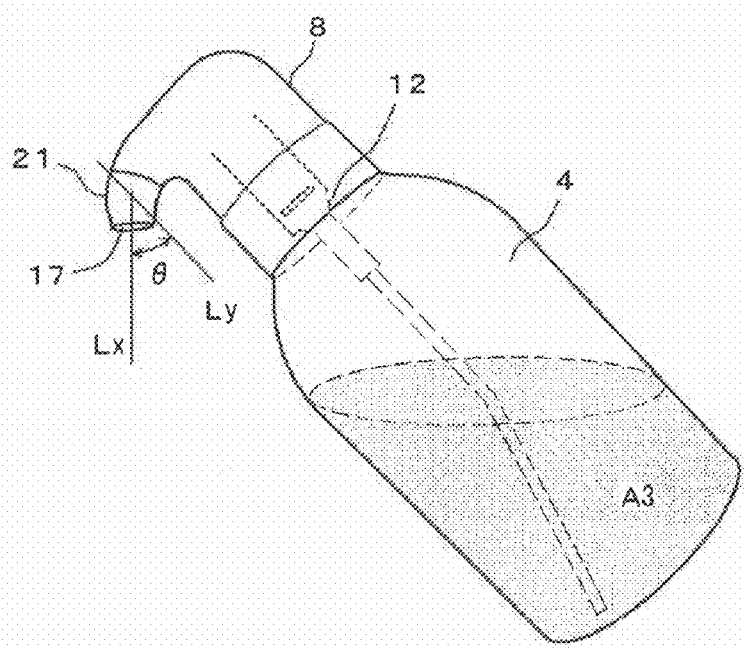

Therefore, as illustrated in FIG. 6(a), the tip of the discharge outlet 17 is preferably made to have an angle θ, formed between the axis Lx perpendicular to the aperture face of the discharge outlet 17 and the vertical direction Ly when the squeeze container 6 is stood upright, of 80° to 10° by either attaching a downward-facing discharge nozzle 21 or by integrally forming such a discharge nozzle 21 with the head portion 8. This angle θ is more preferably 65° to 20°, and especially preferably 50° to 30°. As illustrated in FIG. 6(b), because a user usually does not tilt the axis Lx perpendicular to the aperture face of the discharge outlet 17 more than the orientation of the vertical direction, by forming such a discharge outlet 17, the air induct path 12 can be prevented from being covered by the mixed solution A3 when the user tilts the container body 4.

EXAMPLES

The following examples are all carried out at room temperature (25° C.)

Test Example 1

(1) Preparation of Two-Part Hair Cosmetic for Hair Dyeing

The first and second agents of the two-agent type composition for hair dyeing having the blended compositions shown in Tables 1 and 2 can be prepared. The viscosity and pH of each of the first and second agents can be measured. Also measured are the viscosity and pH of mixed solutions in a 4:6 mass ratio of the first and second agents. Viscosity is measured using a B-type rotary viscometer with the No. 1 rotor by rotating at 30 rpm for 1 minute. The pH is measured using a pH meter (F-52, electrode 9611-10D, manufactured by Horiba, Ltd.). These results are shown in Table 3.

On the other hand, the squeeze container 6 of FIG. 1B is constituted of a flexible container body 4 and a squeeze foamer ("S1 Squeeze Foamer" manufactured by Daiwa Can Company) to serve as a squeeze container for use in Test Example 1. This flexible container body 4 is made from polypropylene (PP), and has a resin weight of 17 g and an interior volume of 210 mL. The ⅔ power coefficient α calculated from this resin weight and interior volume ($\alpha = w/V^{2/3}$) is 0.46. The cross-sectional profile at a height 55 mm from the bottom, which corresponds to the middle in the height direction of the container body 4, is an ellipse (61 mm major axis, 44 mm minor axis, 21 cm$^2$ area). The ratio La/Lb of minor axis La to major axis Lb is 0.72.

Furthermore, as the homogenizing means in the squeeze foamer 5, a 150 mesh net is provided on the gas-liquid mixing chamber 11 side and a 200 mesh net is provided on the discharge outlet 17 side. The aperture area (total of 3 locations) of the narrowest portion of the air induct path 12 in the squeeze foamer is 0.27 mm$^2$, and the ratio between this aperture area and the flow path cross-sectional area of the dip tube 13 is 0.086.

(2) Discharge Properties Evaluation

The above-described squeeze container is charged with 40 g of the first agent and 60 g of the second agent. Shaking is then carried out by moving the container body from a roughly upright state to an inverted state, and then once again returning to a roughly upright state at a rate of 3 times in 10 seconds. This shaking is carried out 5 times. As a result of this shaking, the mixed solution of the first and second agents is mixed without producing a foam. A squeeze foamer is then attached.

Next, the squeeze container is stood upright, and then squeezed 30 mm by the same method as the below-described thrust measurement for about 2 seconds per squeeze to discharge the foamy mixed solution. The (a) discharge amount per squeeze is evaluated in the following manner, and (b) the gas-liquid mixing ratio is measured in the following manner to evaluate the foam quality of the discharged foam.

Furthermore, the (c) thrust and the (d) recovery properties during squeezing are evaluated as follows.

These results are shown in Table 4.

(a) Discharge Amount Per Squeeze

The mass of the mixed solution discharged by repeatedly squeezing 3 times from the initial time is measured to determine the discharge amount (g) per squeeze. Evaluation is carried out using this value as follows.

"AA": 3 g or more
"A": 2 g or more to less than 3 g
"B": 1 g or more to less than 2 g
"C": less than 1 g (b) Gas-Liquid Mixing Ratio 20 g is discharged from the squeeze container into a 1,000 mL graduated cylinder. The gas-liquid mixing ratio (mL/g) is found by dividing the total volume (mL) of the foam and the liquid 1 minute after the initial discharge by 20 g. Using this value, the evaluation is carried out as follows.

"AA": 20 mL/g or more to less than 30 mL/g
"A": 15 mL/g or more to less than 20 mL/g, or 30 mL/g or more to less than 40 mL/g
"B": 10 mL/g or more to less than 15 mL/g, or 40 mL/g or more to less than 50 mL/g
"C": less than 10 mL/g, or 50 mL/g or more The evaluated criteria are determined from the perspectives of the amount placed on the hand, and the liquor ratio when coated on the hair. However, cases where the volume of liquid immediately after discharging 20 g is 3 mL or more are all evaluated as "C" since such cases are problematic as the liquid would trickle down when taken in the hand.

(c) Thrust

A foam of the mixed solution is discharged by squeezing at 25° C. The middle portion (position 55 mm from the bottom of the container body 4) of a height Lh of the container body 4 is squeezed 15 mm/sec to a distance ½ of the minor axis in the minor axis direction from both opposing sides of the container body 4 with a rod-like member made of stainless steel having a tip with a diameter of 15 mm and a height of 5 mm in a roughly dome shape. The maximum load at the first squeeze is measured. From this measured value, evaluation is carried out as follows.

"AA": less than 5 Kgf
"A": 5 Kgf or more to less than 5.5 Kgf
"B": 5.5 Kgf or more to less than 6 Kgf
"C": 6 Kgf or more (d) Recovery Properties After the measurement of (c) is carried out, the time taken for the container body to return to its original shape when the load is released is measured.

"AA": less than 0.5 seconds
"A": 0.5 seconds or more to less than 1 second
"B": 1 second or more to less than 3 seconds
"C": 3 seconds or more (an operation to help the container body to return to its original shape is required, such as applying pressure in the major axis direction)

Test Examples 1-2 to 1-6

The initial filled amount in the container of the mixed solution (mass ratio of the first and second agents of 4:6) is changed as shown in Table 4 while keeping the same ratio. Then, including each of the evaluations in Test Example 1, the above-described discharge properties are evaluated in the initial state. The results are shown in Table 4.

TABLE 1

| First agent blend component | Blend amount (mass %) |
| --- | --- |
| Meta-aminophenol | 0.03 |
| Toluene-2,5-diamine | 0.18 |
| Resorcin | 0.07 |
| 5-Amino-ortho-cresol | 0.04 |
| 2,4-Diaminophenoxyethanol hydrochloride | 0.06 |
| Strong ammonia water | 6.0 |
| Ammonium hydrogencarbonate | 10.5 |
| Decylpoly(1.4)glucoside | 6.16 |
| Polyoxyethylene(2) lauryl ether sodium sulfate | 2.7 |
| Polyoxyethylene(9) tridecyl ether | 0.5 |
| Polyoxyethylene(23) lauryl ether | 2.0 |
| Myristyl alcohol | 0.2 |
| Propylene glycol | 4.0 |
| Ethanol | 10.0 |
| Dimethyldiallylammonium chloride/acrylic acid copolymer | 0.4 |

TABLE 1-continued

| First agent blend component | Blend amount (mass %) |
| --- | --- |
| Dimethyldiallylammonium chloride/acrylamide copolymer | 0.5 |
| Royal jelly extract | 0.01 |
| L-arginine | 0.01 |
| Ascorbic acid | 0.4 |
| Sodium sulfite anhydride | 0.5 |
| Tetrasodium edetate dihydrate | 0.1 |
| Perfume | 0.95 |
| Purified water | Balance |
| Viscosity (mPa · s) | 14 |
| pH | 9.1 |

TABLE 2

| Second agent blend component | Blend amount (mass %) |
| --- | --- |
| Hydrogen peroxide water (35%) | 16.3 |
| Polyoxyethylene(2) lauryl ether sodium sulfate | 0.6 |
| Cetanol | 0.48 |
| Myristyl alcohol | 0.28 |
| Oxyquinoline sulfate | 0.04 |
| Hydroxyethane diphosphonic acid | 0.08 |
| Sodium hydroxide solution | (*1) |
| Purified water | Balance |
| Viscosity (mPa · s) | 15 |

(*1): the amount required for adjusting pH to 3.5

TABLE 3

| Mixed solution viscosity (mPa · s) | 7 |
| --- | --- |
| Mixed solution pH | 9.0 |

TABLE 4

| | Test Ex. 1 | Test Ex. 1-2 | Test Ex. 1-3 | Test Ex. 1-4 | Test Ex. 1-5 | Test Ex. 1-6 |
| --- | --- | --- | --- | --- | --- | --- |
| Container body material | PP | ← | ← | ← | ← | ← |
| Container body resin weight | 17 | ← | ← | ← | ← | ← |
| Container body inner volume (mL) | 210 | ← | ← | ← | ← | ← |
| 2/3 Power coefficient (w/V$^{2/3}$) | 0.47 | ← | ← | ← | ← | ← |
| Minor axis La of the torso cross-section of the container body (mm) | 44 | ← | ← | ← | ← | ← |
| Major axis Lb of the torso cross-section of the container body (mm) | 61 | ← | ← | ← | ← | ← |
| Ratio La/Lb of minor axis to major axis | 0.72 | ← | ← | ← | ← | ← |
| Area of the torso cross-section of the container body (cm$^2$) | 21 | ← | ← | ← | ← | ← |
| Homogenizing means (net on the gas-liquid mixing chamber side) roughness (mesh) | 150 | ← | ← | ← | ← | ← |
| Homogenizing means (net on the nozzle side) roughness (mesh) | 200 | ← | ← | ← | ← | ← |
| Air aperture area/Liquid flow path cross-sectional area | 0.086 | ← | ← | ← | ← | ← |
| Air collector aperture area (mm$^2$) | 0.27 | ← | ← | ← | ← | ← |
| Initial filled amount of the mixed solution (mL) | 100 | 88 | 105 | 67 | 143 | 168 |
| Ratio between the initial filled amount of the mixed solution and the inner volume of the container body | 0.48 | 0.42 | 0.50 | 0.32 | 0.68 | 0.80 |
| Discharge properties | | | | | | |
| Gas-liquid mixing ratio | AA 21 mL/g | AA 22 mL/g | AA 21 mL/g | AA 23 mL/g | A 18 mL/g | B 13 mL/g |
| Recovery properties | AA Within 0.5 seconds | AA Within 0.5 seconds | AA Within 0.5 seconds | AA Within 0.5 seconds | AA Within 0.5 seconds | AA Within 0.5 seconds |

From Table 4, it can be seen that for Test Examples 1 to 1-5, which had a ratio between the initial filled volume of the mixed solution and the inner volume of the container body of from 0.30 to 0.70, foam quality can be stabilized, whereas for Test Example 1-6, which has a ratio larger than this, the foam quality is looser and the thrust is higher.

Test Examples 2 to 2-5

Evaluation of the discharge properties is carried in the same manner as in Test Example 1, except that the used container body of the squeeze container has a different ratio between the minor axis and major axis of the torso cross-section as shown in Table 5, and that the evaluation is carried out at the point where the mixed solution in the container body is 80 g. The results are shown in Table 5.

From Table 5, it can be seen that for Test Examples 2 to 2-4, in which the ratio between minor axis and major axis was in the range of from 0.50 to 1.0, the recovery properties are better than those for Test Example 2-5, in which the ratio is lower.

sectional area as shown in Table 6, and that the evaluation is carried out at the point where the mixed solution in the container body is 80 g. The results are shown in Table 6.

TABLE 5

|  | Test Ex. 2 | Test Ex. 2-2 | Test Ex. 2-3 | Test Ex. 2-4 | Test Ex. 2.5 |
|---|---|---|---|---|---|
| Container body material | PP | ← | ← | ← | ← |
| Container body resin weight | 17 | ← | ← | ← | ← |
| Container body inner volume (mL) | 210 | ← | ← | ← | ← |
| 2/3 Power coefficient (w/$V^{2/3}$) | 0.47 | ← | ← | ← | ← |
| Minor axis La of the torso cross-section of the container body (mm) | 42 | 46 | 37 | 52 | 33 |
| Major axis Lb of the torso cross-section of the container body (mm) | 64 | 58 | 72 | 52 | 82 |
| Ratio La/Lb of minor axis to major axis | 0.65 | 0.80 | 0.52 | 1.0 | 0.40 |
| Area of the torso cross-section of the container body (cm$^2$) | 21 | ← | ← | ← | ← |
| Homogenizing means (net on the gas-liquid mixing chamber side) roughness (mesh) | 150 | ← | ← | ← | ← |
| Homogenizing means (net on the nozzle side) roughness (mesh) | 200 | ← | ← | ← | ← |
| Air aperture area/Liquid flow path cross-sectional area | 0.086 | ← | ← | ← | ← |
| Air collector aperture area (mm$^2$) | 0.27 | ← | ← | ← | ← |
| Initial filled amount of the mixed solution (mL) | 100 | ← | ← | ← | ← |
| Ratio between the initial filled amount of the mixed solution and the inner volume of the container body | 0.48 | ← | ← | ← | ← |
| Discharge properties |  |  |  |  |  |
| Discharge amount per squeeze | AA 3.2 g | A 2.9 g | A 2.7 g | B 1.6 g | B 1.8 g |
| Gas-liquid mixing ratio | AA 22 mL/g | AA 22 mL/g | AA 22 mL/g | AA 22 mL/g | AA 22 mL/g |
| Thrust | AA 4.9 Kgf | A 5.3 Kgf | AA 4.8 Kgf | A 5.5 Kgf | AA 4.5 Kgf |
| Recovery properties | AA Within 0.5 seconds | AA Within 0.5 seconds | A 0.9 seconds | AA Within 0.5 seconds | B 2 seconds |

Test Examples 3 to 3-6

Evaluation of the discharge properties is carried in the same manner as in Test Example 1, except that the container body of the squeeze container has a different torso cross- From Table 6, it can be seen that for Test Examples 3 to 3-4, in which the torso cross-sectional area of the container body is in the range of from 12 cm$^2$ to 30 cm$^2$, the discharge amount of 1 squeeze is larger than for both Test Example 3-5, in which the cross-sectional area is smaller, and Test Example 3-6, in which the cross-sectional area is larger.

TABLE 6

|  | Test Ex. 3 | Test Ex. 3-2 | Test Ex. 3-3 | Test Ex. 3-4 | Test Ex. 3-5 | Test Ex. 3-6 |
|---|---|---|---|---|---|---|
| Container body material | PP | ← | ← | ← | ← | ← |
| Container body resin weight | 17 | ← | ← | ← | ← | ← |
| 2/3 Power coefficient (w/$V^{2/3}$) | 0.47 | ← | ← | ← | ← | ← |
| Container body inner volume (mL) | 210 | ← | ← | ← | ← | ← |
| Minor axis La of the torso cross-section of the container body (mm) | 41 | 47 | 35 | 52 | 30 | 55 |
| Major axis Lb of the torso cross-section of the container body (mm) | 56 | 65 | 48 | 72 | 42 | 76 |
| Ratio La/Lb of minor axis to major axis | 0.72 | ← | ← | ← | ← | ← |
| Area of the torso cross-section of the container body (cm$^2$) | 18 | 24 | 13 | 29 | 10 | 33 |
| Homogenizing means (net on the gas-liquid mixing chamber side) roughness (mesh) | 150 | ← | ← | ← | ← | ← |
| Homogenizing means (net on the nozzle side) roughness (mesh) | 200 | ← | ← | ← | ← | ← |
| Air aperture area/Liquid flow path cross-sectional area | 0.086 | ← | ← | ← | ← | ← |
| Air collector aperture area (mm$^2$) | 0.27 | ← | ← | ← | ← | ← |
| Initial filled amount of the mixed solution (mL) | 100 | ← | ← | ← | ← | ← |
| Ratio between the initial filled amount of the mixed solution and the inner volume of the container body | 0.48 | ← | ← | ← | ← | ← |
| Discharge properties |  |  |  |  |  |  |
| Discharge amount per squeeze | AA 3.1 g | AA 3.1 g | A 2.2 g | A 2.8 g | B 1.4 g | B 1.82 g |

TABLE 6-continued

|  | Test Ex. 3 | Test Ex. 3-2 | Test Ex. 3-3 | Test Ex. 3-4 | Test Ex. 3-5 | Test Ex. 3-6 |
|---|---|---|---|---|---|---|
| Gas-liquid mixing ratio | AA 22 mL/g | AA 22 mL/g | AA 22 mL/g | AA 22 mL/g | AA 22 mL/g | AA 22 mL/g |
| Recovery properties | AA Within 0.5 seconds | AA Within 0.5 seconds | AA Within 0.5 seconds | AA Within 0.5 seconds | AA Within 0.5 seconds | AA Within 0.5 seconds |

Test Examples 4 to 4-6

Evaluation of the discharge properties is carried in the same manner as in Test Example 1, except that the container body of the squeeze container has a different ratio between the aperture area of the narrowest portion of the air induct path and the dip tube as shown in Table 7, and that the evaluation is carried out at the point where the mixed solution in the container body is 80 g. The results are shown in Table 7.

From Table 7, it can be seen that good foam quality is obtained for Test Examples 4 to 4-4, in which this ratio is in the range of 0.05 to 0.25.

In contrast, it can be seen that if this ratio is small as in Test Example 4-5, although the discharge amount increases, the foam is looser, while if this ratio is large as in Test Example 4-6, the volume of the liquid when measuring the gas-liquid mixing ratio is 3 mL or more, so that the discharge amount is reduced.

Test Examples 5 to 5-6

Evaluation of the discharge properties is carried in the same manner as in Test Example 1, except that the 2/3 power coefficient α calculated from the resin weight and the inner volume of the container body ($\alpha = w/V^{2/3}$) is different as shown in Table 8, and that the evaluation is carried out at the point where the mixed solution in the container body is 80 g. The results are shown in Table 8.

From Table 8, it can be seen that for Test Examples 5 to 5-4, in which the 2/3 power coefficient is in the range of from 0.40 to 0.60, the discharging is carried out with a low thrust and with good recovery properties.

In contrast, it can be seen that if this ratio is low due to a low resin weight of the container body as in Test Example 5-5, although the thrust is small, recovery does not take place easily, while if this ratio is large due to a large resin weight as in Test Example 5-6, although recovery takes place easily, a large thrust is required.

TABLE 7

|  | Test Ex. 4 | Test Ex. 4-2 | Test Ex. 4-3 | Test Ex. 4-4 | Test Ex. 4-5 | Test Ex. 4-6 |
|---|---|---|---|---|---|---|
| Container body material | PP | ← | ← | ← | ← | ← |
| Container body resin weight | 17 | ← | ← | ← | ← | ← |
| Container body inner volume (mL) | 210 | ← | ← | ← | ← | ← |
| 2/3 Power coefficient ($w/V^{2/3}$) | 0.47 | ← | ← | ← | ← | ← |
| Minor axis La of the torso cross-section of the container body (mm) | 44 | ← | ← | ← | ← | ← |
| Major axis Lb of the torso cross-section of the container body (mm) | 61 | ← | ← | ← | ← | ← |
| Ratio La/Lb of minor axis to major axis | 0.72 | ← | ← | ← | ← | ← |
| Area of the torso cross-section of the container body (cm$^2$) | 21 | ← | ← | ← | ← | ← |
| Homogenizing means (net on the gas-liquid mixing chamber side) roughness (mesh) | 150 | ← | ← | ← | ← | ← |
| Homogenizing means (net on the nozzle side) roughness (mesh) | 200 | ← | ← | ← | ← | ← |
| Air aperture area/Liquid flow path cross-sectional area | 0.07 | 0.09 | 0.05 | 0.24 | 0.04 | 0.3 |
| Air collector aperture area (mm$^2$) | 0.27 | ← | ← | ← | ← | ← |
| Initial filled amount of the mixed solution (mL) | 100 | ← | ← | ← | ← | ← |
| Ratio between the initial filled amount of the mixed solution and the inner volume of the container body | 0.48 | ← | ← | ← | ← | ← |
| Discharge properties |  |  |  |  |  |  |
| Discharge amount per squeeze | AA 3.5 g | AA 3.1 g | AA 3.8 g | A 2.1 g | AA 3.9 g | C 0.9 g |
| Gas-liquid mixing ratio | AA 20 mL/g | AA 23 mL/g | A 17 mL/g | AA 25 mL/g | C 9 mL/g | C Liquid, 3 mL or more |
| Recovery properties | AA Within 0.5 seconds | AA Within 0.5 seconds | AA Within 0.5 seconds | AA Within 0.5 seconds | AA Within 0.5 seconds | AA Within 0.5 seconds |

TABLE 8

|  | Test Ex. 5 | Test Ex. 5-2 | Test Ex. 5-3 | Test Ex. 5-4 | Test Ex. 5-5 | Test Ex. 5-6 |
| --- | --- | --- | --- | --- | --- | --- |
| Container body material | PP | ← | ← | ← | ← | ← |
| Container body resin weight | 16 | 19 | 15 | 20 | 11 | 25 |
| Container body inner volume (mL) | 210 | ← | ← | ← | ← | ← |
| 2/3 Power coefficient (w/$V^{2/3}$) | 0.46 | 0.54 | 0.42 | 0.58 | 0.30 | 0.70 |
| Minor axis La of the torso cross-section of the container body (mm) | 44 | ← | ← | ← | ← | ← |
| Major axis Lb of the torso cross-section of the container body (mm) | 60 | ← | ← | ← | ← | ← |
| Ratio La/Lb of minor axis to major axis | 0.72 | ← | ← | ← | ← | ← |
| Area of the torso cross-section of the container body ($cm^2$) | 21 | ← | ← | ← | ← | ← |
| Homogenizing means (net on the gas-liquid mixing chamber side) roughness (mesh) | 150 | ← | ← | ← | ← | ← |
| Homogenizing means (net on the nozzle side) roughness (mesh) | 200 | ← | ← | ← | ← | ← |
| Air aperture area/Liquid flow path cross-sectional area | 0.086 | ← | ← | ← | ← | ← |
| Air collector aperture area ($mm^2$) | 0.27 | ← | ← | ← | ← | ← |
| Initial filled amount of the mixed solution (mL) | 100 | ← | ← | ← | ← | ← |
| Ratio between the initial filled amount of the mixed solution and the inner volume of the container body | 0.48 | ← | ← | ← | ← | ← |
| Discharge properties |  |  |  |  |  |  |
| Discharge amount per squeeze | AA 3.2 g | AA 3.2 g | AA 3.2 g | AA 3.2 g | AA 3.2 g | AA 3.2 g |
| Gas-liquid mixing ratio | AA 22 mL/g | AA 22 mL/g | AA 22 mL/g | AA 22 mL/g | AA 22 mL/g | AA 22 mL/g |
| Thrust | AA 4.9 Kgf | A 5.39 Kgf | AA 4.4 Kgf | A 5.59 Kgf | AA 4.0 Kgf | C 7.0 Kgf |
| Recovery properties | AA Within 0.5 seconds | AA Within 0.5 seconds | A 1 second | AA Within 0.5 seconds | C Did not return | AA Within 0.5 seconds |

INDUSTRIAL APPLICABILITY

The two-part hair cosmetic for hair dyeing or bleaching of the present invention can be applied for hair dyeing or bleaching.

The invention claimed is:

1. A hair cosmetic for hair dyeing or bleaching, comprising a mixed solution inside of a squeeze container for discharging a foam, wherein said mixed solution is prepared by mixing a first agent comprising an alkaline agent and a second agent comprising hydrogen peroxide, wherein:
   at least one of said first or second agents comprises a foaming agent,
   said mixed solution of said first and second agents has a viscosity (25° C.) of from 1 mPa·s to 100 mPa·s,
   said squeeze container has a container body and a squeeze foamer,
   said squeeze foamer has a gas-liquid mixing chamber for causing said mixed solution to foam by mixing air in said container body with said mixed solution, foam homogenizing means for homogenizing a foam of said mixed solution which has been made to foam in said gas-liquid mixing chamber, and a discharge outlet for discharging a homogenized foam, and
   a ratio between an initial total volume of said mixed solution and an inner volume of said container body (total volume/inner volume) is in a range of from 0.30 to 0.60.

2. A cosmetic for hair dyeing or bleaching according to claim 1, wherein
   said container body has a torso outer shape with a cross-section with a ratio of minor axis to major axis at a middle portion in a height direction of said container body of from 0.50 to 1.0.

3. A hair cosmetic for hair dyeing or bleaching according to claim 1, wherein
   said container body has a torso outer shape with a cross-section with an area at a middle portion in a height direction of said container body of from 12 $cm^2$ to 30 $cm^2$.

4. A hair cosmetic for hair dyeing or bleaching according to claim 1, wherein said container body is formed from a polyolefin resin, and a ratio between a resin weight w (g) of the container body and ⅔ power of an inner volume V of the container body (w/$V^{2/3}$), is in a range of from 0.40 to 0.60.

5. A hair cosmetic for hair dyeing or bleaching according to claim 1, wherein said squeeze foamer comprises an air induct path which allows an interior space of said container body and a gas-liquid mixing chamber to be in communication with each other, and a dip tube which extends from said the gas-liquid mixing chamber to said container body bottom side, and wherein a ratio between an aperture area of the narrowest portion of the air induct path and a flow path cross-sectional area of the dip tube, aperture area of the narrowest portion/flow path cross-sectional area, is in a range of from 0.05 to 0.25.

6. A hair cosmetic for hair dyeing or bleaching according to claim 1, wherein said discharge outlet is formed such that an angle formed between an axis perpendicular to an aperture face of the discharge outlet and a vertical direction when the squeeze container is stood upright is set in a range of from 10° to 80°.

7. A cosmetic for hair dyeing or bleaching according to claim 1 wherein said discharge outlet is formed such that an angle formed between an axis perpendicular to an aperture face of the discharge outlet and a vertical direction when the squeeze container is stood upright is set in a range of from 20° to 65°.

8. A kit for hair dyeing or bleaching comprising:
   (A) a two-part hair dye or bleach composition comprising (i) a first agent comprising an alkaline agent and (ii) a second agent comprising hydrogen peroxide; and (B) a squeeze container for discharging a foam, wherein, at least one of said first or second agents comprises a foaming agent, a mixed solution formed by mixing said first and second agents has a viscosity (25° C.) of from 1 mPa·s to 100 mPa·s, said squeeze container has a container body and a squeeze foamer, said squeeze foamer has a gas-liquid mixing chamber for causing a mixed solution formed by mixing said first and second agents to foam by mixing air with said mixed solution, foam homogenizing means for homogenizing a foam of said mixed solution, and a discharge outlet for discharging a homogenized foam, and a ratio between an initial total volume of said mixed solution formed by mixing said first and second agents and an inner volume of said container body (total volume/inner volume) is in a range of from 0.30 to 0.60.

9. A kit according to claim 8, wherein said container body has a torso outer shape with a cross-section with a ratio of minor axis to major axis at a middle portion in a height direction of said container body of from 0.50 to 1.0.

10. A kit according to claim 8, wherein said container body has a torso outer shape with a cross-section with an area at a middle portion in a height direction of said container body of from 12 cm$^2$ to 30 cm$^2$.

11. A kit according to claim 8, wherein said container body is formed from a polyolefin resin, and a ratio between a resin weight w (g) of the container body and ⅔ power of an inner volume V of the container body (w/V$^{2/3}$), is in a range of from 0.40 to 0.60.

12. A kit according to claim 8, wherein said squeeze foamer comprises an air induct path which allows an interior space of said container body and a gas-liquid mixing chamber to be in communication with each other, and a dip tube which extends from said the gas-liquid mixing chamber to said container body bottom side, and wherein a ratio between an aperture area of the narrowest portion of the air induct path and a flow path cross-sectional area of the dip tube, aperture area of the narrowest portion/flow path cross-sectional area, is in a range of from 0.05 to 0.25.

13. A kit according to claim 8, wherein said discharge outlet is formed such that an angle formed between an axis perpendicular to an aperture face of the discharge outlet and a vertical direction when the squeeze container is stood upright is set in a range of from 10° to 80°.

14. A kit according to claim 8, wherein said discharge outlet is formed such that an angle formed between an axis perpendicular to an aperture face of the discharge outlet and a vertical direction when the squeeze container is stood upright is set in a range of from 20° to 65°.

15. A method for preparing a hair dyeing or bleaching cosmetic comprising:

mixing a first agent comprising an alkaline agent and a second agent comprising hydrogen peroxide inside of a squeeze container, to obtain a mixed solution, wherein at least one of said first or second agents comprises a foaming agent, said mixed solution has a viscosity (25° C.) of from 1 mPa·s to 100 mPa·s, said squeeze container has a container body and a squeeze foamer, said squeeze foamer has a gas-liquid mixing chamber for causing said mixed solution to foam by mixing air with said mixed solution, foam homogenizing means for homogenizing foam of said mixed solution which has been made to foam in said gas-liquid mixing chamber, and a discharge outlet for discharging a homogenized foam, and a ratio between an initial total volume of said first and second agents after mixing and an inner volume of said container body (total volume/inner volume) is in a range of from 0.30 to 0.60.

16. A method for dyeing or bleaching hair comprising:

(a) mixing a first agent comprising an alkaline agent and a second agent comprising hydrogen peroxide inside of a squeeze container, to obtain a mixed solution, wherein at least one of said first or second agents comprises a foaming agent, said mixed solution has a viscosity (25° C.) of from 1 mPa·s to 100 mPa·s, said squeeze container has a container body and a squeeze foamer, said squeeze foamer has a gas-liquid mixing chamber for causing said mixed solution to foam by mixing air with said mixed solution, foam homogenizing means for homogenizing foam of said mixed solution which has been made to foam in said gas-liquid mixing chamber, and a discharge outlet for discharging a homogenized foam, and a ratio between an initial total volume of said first and second agents after mixing and an inner volume of said container body (total volume/inner volume) is in a range of from 0.30 to 0.60;

(b) discharging a homogenized foam of said mixed solution; and (c) applying said homogenized foam to hair.

17. A method according to claim 16, wherein said container body has a torso outer shape with a cross-section with a ratio of minor axis to major axis at a middle portion in a height direction of said container body of from 0.50 to 1.0.

18. A method according to claim 16, wherein said container body has a torso outer shape with a cross-section with an area at a middle portion in a height direction of said container body of from 12 cm$^2$ to 30 cm$^2$.

19. A method according to claim 16, wherein said container body is formed from a polyolefin resin, and a ratio between a resin weight w (g) of the container body and ⅔ power of an inner volume V of the container body (w/V$^{2/3}$), is in a range of from 0.40 to 0.60.

20. A method according to claim 16, wherein said squeeze foamer comprises an air induct path which allows an interior space of said container body and a gas-liquid mixing chamber to be in communication with each other, and a dip tube which extends from said the gas-liquid mixing chamber to said container body bottom side, and wherein a ratio between an aperture area of the narrowest portion of the air induct path and a flow path cross-sectional area of the dip tube, aperture area of the narrowest portion/flow path cross-sectional area, is in a range of from 0.05 to 0.25.

21. A method according to claim 16, wherein said discharge outlet is formed such that an angle formed between an axis perpendicular to an aperture face of the discharge outlet and a vertical direction when the squeeze container is stood upright is set in a range of from 10° to 80°.

22. A method according to claim 16, wherein said discharge outlet is formed such that an angle formed between an axis perpendicular to an aperture face of the discharge outlet and a vertical direction when the squeeze container is stood upright is set in a range of from 20° to 65°.

23. A cosmetic for hair dyeing or bleaching according to claim 1, wherein said ratio between said initial total volume of said mixed solution and said inner volume of said container body (total volume/inner volume) is in a range of from 0.40 to 0.60.

24. A cosmetic for hair dyeing or bleaching according to claim 1, wherein said ratio between said initial total volume of said mixed solution and said inner volume of said container body (total volume/inner volume) is in a range of from 0.35 to 0.55.

25. A kit according to claim 8, wherein said ratio between said initial total volume of said mixed solution and said inner volume of said container body (total volume/inner volume) is in a range of from 0.40 to 0.60.

26. A kit according to claim 8, wherein said ratio between said initial total volume of said mixed solution and said inner volume of said container body (total volume/inner volume) is in a range of from 0.35 to 0.55.

27. A method according to claim 16, wherein said ratio between said initial total volume of said mixed solution and said inner volume of said container body (total volume/inner volume) is in a range of from 0.40 to 0.60.

28. A method according to claim 16, wherein said ratio between said initial total volume of said mixed solution and said inner volume of said container body (total volume/inner volume) is in a range of from 0.35 to 0.55.

* * * * *